United States Patent
Attala et al.

(10) Patent No.: US 10,835,521 B2
(45) Date of Patent: Nov. 17, 2020

(54) NEUROPROTECTIVE CB₂ RECEPTOR AGONISTS

(71) Applicant: THE CLEVELAND CLINIC FOUNDATION, Cleveland, OH (US)

(72) Inventors: Mohamed Naguib Attala, Cleveland, OH (US); David L. Brown, Westlake, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 275 days.

(21) Appl. No.: 14/912,647

(22) PCT Filed: Jul. 12, 2013

(86) PCT No.: PCT/US2013/050184
§ 371 (c)(1),
(2) Date: Feb. 18, 2016

(87) PCT Pub. No.: WO2014/011949
PCT Pub. Date: Jan. 16, 2014

(65) Prior Publication Data
US 2016/0193201 A1    Jul. 7, 2016

Related U.S. Application Data

(60) Provisional application No. 61/671,277, filed on Jul. 13, 2012.

(51) Int. Cl.
| | |
|---|---|
| *A61K 31/4525* | (2006.01) |
| *A61P 25/28* | (2006.01) |
| *A61K 31/00* | (2006.01) |
| *A61K 31/343* | (2006.01) |

(52) U.S. Cl.
CPC .......... *A61K 31/4525* (2013.01); *A61K 31/00* (2013.01); *A61K 31/343* (2013.01); *A61P 25/28* (2018.01)

(58) Field of Classification Search
CPC .. A61K 31/4525; A61K 31/343; A61K 31/00; A61P 25/28
See application file for complete search history.

(56) References Cited

U.S. PATENT DOCUMENTS

| | | | |
|---|---|---|---|
| 5,605,906 A * | 2/1997 | Lau | C07D 221/12 514/298 |
| 5,684,002 A | 11/1997 | Scherz et al. | |
| 5,948,777 A | 9/1999 | Bender et al. | |
| 5,981,776 A | 11/1999 | Diaz et al. | |
| 2005/0267161 A1 | 12/2005 | Lange et al. | |
| 2007/0099990 A1 | 5/2007 | Ohkawa et al. | |
| 2007/0105893 A1 * | 5/2007 | Page | C07D 235/12 514/303 |
| 2009/0124608 A1 * | 5/2009 | Prather | A61K 31/454 514/230.5 |
| 2010/0004244 A1 | 1/2010 | Galve-Roperh et al. | |
| 2010/0204220 A1 | 8/2010 | Attala et al. | |

FOREIGN PATENT DOCUMENTS

| | | |
|---|---|---|
| EP | 0816352 B1 | 2/2001 |
| JP | 20100533724 A | 10/2010 |
| WO | 9729100 A1 | 8/1997 |
| WO | 9824778 A1 | 6/1998 |
| WO | 2005080349 A1 | 9/2005 |
| WO | 2006097193 A1 | 9/2006 |

OTHER PUBLICATIONS

Naguib et al. (British Journal of Pharmacology, 2008, 155, 1104-1116).*
Ashton et al., Current Neuropharmacology, 2007, 5, 73-80 (Year: 2007).*
Wu et al. (Neurobiology of Aging, 34, 2013, 791-804, published online Jul. 12, 2012) (Year: 2012).*
Akiyama, Haruhiko, et al. "Inflammation and Alzheimer's disease." Neurobiology of aging 21.3 (2000): 383-421.
Ashton , John C., and Michelle Glass. "The cannabinoid CB2 receptor as a target for inflammation-dependent neurodegeneration." Current neuropharmacology 5.2 (2007): 73-80.
Baker, David, et al. "Cannabinoids control spasticity and tremor in a multiple sclerosis model." Nature 404.6773 (2000) 84-87.
Berghuis, Paul, et al. "Hardwiring the brain: endocannabinoids shape neuronal connectivity." Science 316.5828 (2007): 1212-1216.
Blazquez, Cristina, et al. "Cannabinoid receptors as novel targets for the treatment of melanoma." The FASEB journal 20.14 (2006): 26333-2635.

(Continued)

*Primary Examiner* — Theodore R. West
(74) *Attorney, Agent, or Firm* — Tarolli, Sundheim, Covell & Tummino LLP

(57) ABSTRACT

A method of treating or preventing a neuroinflammatory and/or neurodegenerative disease in a subject by administering a pharmaceutically effective amount of a CB2 receptor agonist is described. The CB2 receptor agonist can be a compound according to formula I (structurally represented) or a pharmaceutically acceptable salt thereof, with R1 and R2 functional groups as defined herein. Administration of the CB2 receptor agonist activates CB2 receptors in the microglia, and can restore synaptic plasticity, cognition, and memory in subjects having elevated levels of amyloid-13 peptide in the brain.

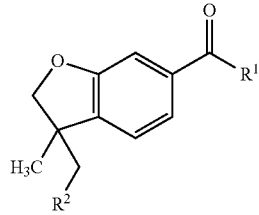

I

8 Claims, 4 Drawing Sheets

(56) References Cited

OTHER PUBLICATIONS

Campillo, Nuna E., and J. A. Paez, "Cannabinoid system in neurodegeneration: new perspectivies in Alzheimer's disease." Mini reviews in medicinal chemistry 9.5 (2009): 539-559.
Chaplan, S. R., et al. "Quantitative assessment of tactle allodynia in the rat paw." Journal of neuroscience methods 53.1 (1994): 55-63.
Chen, B., et al. "Effect of synthetic cannabinoid HU210 on memory deficits and neuropathology in Alzheimer's disease mouse model." Current Alzheimer Research 7.3 (2010): 256-261.
Chevaleyre, Vivien. Kanji A. Takahashi, and Pablo E. Castillo. "Endocannabinoid-mediated synaptic plasticity in the CNS." Annu. Rev. Neurosci. 29 (2006): 37-76.
Crowley, Vivion EF, Giles SH Yeo, and Stephen O'Rahilly. "Obesity therapy: altering the energy intake-and-expenditure balance sheet." Nature reviews Drug discovery 1.4 (2002): 276-286.
Davis, Tyler A., Todd K. Hyster, and Tomislav Rovis, "Rhodium (III)-Catalyzed Intramolecular Hydroarylation, Amidoarylation and Heck-type Reaction: Three Distinct Pathways Determined by an Amide Directing Group." Angewandte Chemie International Edition 52.52 (2013): 14181-14185.
Diaz, Philippe, et al. "2. 3-Dihydro-1-Benzofuran Deriviatives as a Series of Potent Slective Cannabinoid Receptor 2 Agonist: Design, Synthesis, and Binding Mode Prediction through Ligand-Steered Modeling." ChemMedChem 4.10 (2009): 1615-1629.
Diaz, Philippe, et al. "Preparation of heterocyclic diaryl compounds and pharmaceutical and cosmetic compostions containg them" Centre International de Recherches Dermatologiques Galderma, pp. 1-8.
Diaz, Philippe, et al. "New synthetic retinoids obtained by palladium-catalyzed tandem cyclisation-hydride capture process." Tetrahedron 54.18 (1998): 4579-4590.
Dixon, W. J. "The up-and-down method for small samples." Journal of the American Statistical Association 60.312 (1965): 967-978.
Ehrahart, Jared. et al. "Stimulation of cannabinoid receptor 2 (CB2) suppresses microglial activation." Journal of Neuroinflammation 2.1 (2005): 29.
El Khoury, Joseph, et al. "Scavenger receptor-mediated adhesion of microglia to β-amyloid fibrils." Nature 382.6593 (1996): 716-719.
Eng, Lawrence F. "Glial fibrillary acidic protein (GFAP): the major protein of glial intermediate filaments in differentiated astrocytes." Journal of Neuroimmunology 8 (1985): 203-214.
Extended European Search Report for Application No. 13816574.1, dated Mar. 23, 2016; pp. 1-12.
Ex parte quayle for U.S. Appl. No. 12/668,840, filed Mar. 2, 2010, mailed Sep. 14, 2012, pp. 1-4.
Ferandin. Yoan, et al. "3'-substituted 7-halogenoindirubins, a new class of cell death inducing agents." Journal of medicinal chemistry 49.15 (2006): 4638-4649.
Fride, E. "Endocannabinoids in the central nervous system—an overview." Prostaglandins, Leukotrienes and Essential Fatty Acids (PLEFA) 66.2 (2002): 221-233.
Van Gaal, Luc F., et al. "Effects of the cannabinoid-1 receptor blocker rimonabant on weight reduction and cardiovascular risk factors in overweight patients 1-year experience from the RIO-Europe study." The Lancet 365.9468 (2005): 1389-1397.
Gabay, Cem. Céline Lamacchia, and Gaby Palmer. "IL-1 pathways in inflammation and human diseases." Nature Reviews Rheumatology 6.4 (2010): 232-241.
Gaoni, Yechiel and R. Mechoulam. "Isolation, structure, and partial synthesis of an active constituent of hashish." Journal of the American chemical society 86.8 (1964): 1646-1647.
Gatley, S. John, et al. "123 I-labeled AM251: a radiciodinated ligand which binds in vivo to mouse brain cannabinoid CB 1 receptors." European journal of pharmacology 307.3 (1996): 331-338.
Giblin, Gerard MP, et al. "Dicovery of 2-[(2, 4-dichlorophnyl) amino]-N-[(tetrahydro-2 H-pyran-4-yl) methyl]-4-(trifluoromethyl)-5-pyrimidinecarboxamide, a selective CB2 receptor agonist for the treatment of inflammatory pain." Journal of medicinal chemistry 50.11 (2007): 2597-2600.

Guindon, J., and A. G. Hohmann, "Cannabinoid CB2 receptors: a therapeutic target for the treatment of inflammatory and neuropathic pain." British journal of pharmacology 153.2 (2008): 319-334.
Guzman, Manuel. "Cannabinoids: potential anticancer agents." Nature Reviews Cancer 3.10 (2003): 745-755.
Herzberg, U., et al. "The analgesic eflicts of R(+)-WIN 55.212-2 mesylate, a high affinity cannabinoid agonist, in a rat model of neuropathic pain." Neuroscience letters 221.2 (1997): 157-160.
Hosohata, Yoshiaki, et al. "AM630 antagonism of cannabinoid-stimulated [35 S] GTPγS binding in the mouse brain." European journal of pharmacology 321.1 (1997): R1-R3.
Ibrahim, Mohab M., et al. "Activation of CB2 cannabinoid receptors by AM1241 inhibits experimental neuropathic pain: pain inhibition by receptors not present in the CNS." Proceedings of the National Academy of Sciences 100.18 (2003): 10529-10533.
Ibrahim, Mohab M., et al. "CB2 cannabinoid receptor activation produces antinociception by stimulating peripheral release of endogenous opioids." Proceedings of the National Academy of Sciences of the United States of America 102.8 (2005): 3093-3098.
Idris, Aymen I., et al. "Regulation of bone mass, bone loss and osteoclast activity by cannabinoid receptors." Nature medicine 11.7 (2005): 774-779.
Kalsi, Vinay, and Clare J. Fowler. "Therapy Insight bladder dysfunction associated with multiple sclerosis." Nature Clinical Practice Urology 2.10 (2005): 492-501.
Karl, Tim, et al. "The therapeutic potential of the endocannabinoid system for Alzheimer's disease." Expert opinion on therapeutic targets 16.4 (2012): 407-420.
Karsak, Meliha, et al. "Attenuation of allergic contact dermatitis through the endocannabinoid system." science 316.5830 (2007): 1494-1497.
Kathuria, Satish, et al. "Modulation of anxiety through blockade of anandamide hydrolys." Nature medicine 9.1 (2003): 76-81.
Kehl, Lois J., et al. "A cannabinoid agonist differentially attenuates deep tissue hyperalgesia in animal models of cancer and inflammatory muscle pain." Pain 103.1 (2003): 175-186.
Kim, Sun Ho, and Jin Mo Chung. "An experimental model for peripheral neuropathy produced by segmental spinal nerve ligation in the rat." Pain 50.3 (1992): 355-363.
Luo, Zhushou, and Mohamed Naguib. "A synthetic approach for (S)-(3-benzyl-3-methyl-2, 3-dihydro-benzofuran-6-yl)-piperidin-1-yl-methanone, a selective CB2 receptor agonist," Tetrahedron Letters 53.26 (2012): 3316-3318.
MacCarrone, Mauro, et al. "The Endocannabinoid System in Human Keratinocytes Evidence That Anandamide Inhibits Epidermal Differentiation Through CB1 Receptor-Dependent Inhibition of Protein Kinase C, Activating Protein-1, and Transglutaminase." Journal of Biological Chemistry 276.36 (2003): 33896-33903.
Maldonado, Rafael, Olga Valverde, and Fernando Berrendero. "Involvement of the endocannabinoid system in drug addiction." Trends in neurosciences 29.4 (2006): 225-232.
Maresz, Katarzyna, et al. "Direct supression of CNS autoimmune inflammation via the cannabinoid receptor CB1 on neurons and CB2 on autoreactive T cells." Nature medicine 13.4 (2007): 492-497.
Di Marzo, Vincenzo, Maurizio Bifulco, and Luciano De Petrocellis. "The endocannabinoid system and its therapeutic exploitation." Nature reviews Drug discovery 3.9 (2004): 771-784.
Di Marzo, Vincenzo, et al. "Leptin-regulated endocannabinoids are involved in maintaining food intake." Nature 410.6830 (2001): 822-825.
Matsuda, Lisa A., et al. "Structure of a cannabinoid receptor and functional expression of the cloned cDNA." Nature 346.6284 (1990): 561-564.
Meda, Lucia, Pierluigi Baron, and Guglielmo Scarlato. "Glial activation in Alzheimer's disease: the role of Aβ and its associated proteins." Neurobiology of aging 22.6 (2001): 865-893.
Milton, Nathaniel GN. "Anandamide and noladin ether prevent neurotoxicity of the human amyloid-β peptide." Neuroscience letters 332.2 (2002): 127-130.
Mukherjee, Sutapa, et al. "Species comparison and pharmacological characterization of rat and human CB 2 cannabinoid receptors." European journal of pharmacology 505.1 (2004): 1-9.

(56) References Cited

OTHER PUBLICATIONS

Tolon, Rosa Maria, et al. "The activation of cannabinoid CB 2 receptors stimulates in situ and in vitro beta-amyloid removal by human macrophages." Brain research 1283 (2009): 148-154.

Trang, T., M. Sutak, and K. Jhamandas. "Involvement of cannabinoid (CB 1)-receptors in the development and maintenance of opioid tolerance." Neuroscience 146.3 (2007): 1275-1288.

Van Der Stelt, M., et al. "Endocannabinoids and β-amyloid-induced neurotoxicity in vivo: effect of pharmacological elevation of endocannabinoid levels." Cellular and Molecular Life Sciences CMLS 63.12 (2006): 1410-1424.

Vanecek, Jin, "Cellular mechanisms of melatonin action." Physiological reviews 78.3 (1998): 687-721.

Wang, Haibin, et al. "Aberrant cannabinoid signaling impairs oviductal transport of embryos." Nature medicine 10.10 (2004): 1074-1080.

Warms, Catherine A., et al. "Treatments for chronic pain associated with spinal cord injuries: many are tried, few are helpful." The Clinical journal of pain 18.3 (2002): 154-163.

Whiteside, G. T., G. P. Lee, and K. J. Valenzano. "The role of the cannabinoid CB2 receptor in pain transmission and therapeutic potential of small molecule CB2 receptor agonists." Current medicinal chemistry 14.8 (2007): 917-936.

Wilkinson, Jonathan D., and Elizabeth M. Williamson. "Cannabinoids inhibit human keratinocyte proliferation through a non-CB1/CB2 mechanism and have a potential therapeutic value in the treatment of psoriasis." Journal of dermatological science 45.2 (2007): 87-92.

Wu, Jiang, et al. "Activation of the CB 2 receptor system reverses amyloid-induced memory deficiency." Neurobiology of aging 34.3 (2013): 791-804.

Wyss-Coray, Tony. "Inflammation in Alzheimer disease: driving force, bystander or beneficial response?." Nature medicine 12.9 (2006): 1005-1015.

Diaz, Philippe, et al. "6-Methoxy-N-alkyl isatin acylhydrazone derivatives as a novel series of potent selective cannabinoid receptor 2 inverse agonists: design, synthesis, and binding mode prediction." Journal of medicinal chemistry 52.2 (2008): 433-444.

Diaz, Philippe, et al. "2, 3-Dihydro-1-Benzofuran Derivatives as a Series of Potent Selective Cannabinoid Receptor 2 Agonists: Design, Synthesis, and Binding Mode Prediction through Ligand-Steered Modeling." ChemMedChem 4.10 (2009): 1615-1629.

Ehrhart, Jared, et al. "Stimulation of cannabinoid receptor 2 (CB2) suppresses microglial activation." Journal of neuroinflammation 2.1 (2005): 29.

Kim, Kathline, et al. "AM1241, a cannabinoid CB 2 receptor selective compound, delays disease progression in a mouse model of amyotrophic lateral sclerosis." European journal of pharmacology 542.1 (2006): 100-105.

Naguib, M., et al. "MDA7: a novel selective agonist for CB2 receptors that prevents allodynia in rat neuropathic pain models." British journal of pharmacology 155.7 (2008): 1104-1116.

Ramirez, Belén G., et al. "Prevention of Alzheimer's disease pathology by cannabinoids: neuroprotection mediated by blockade of microglial activation." The Journal of Neuroscience 25.8 (2005): 1904-1913.

Torres, E. et al, "Research on Neurochemistry Reported by E. Torres, et al", Pain & Central Nervous System Week, Expanded Report, p. 292, Apr. 26, 2010.

International Search Report and Written Opinion for PCT/US13/50184, dated Jul. 13, 2013, pp. 1-11.

Blazquez, Cristina, et al. "Cannabinoid receptors as novel targets for the treatment of melanoma." The FASEB journal 20.14 (2006): 2633-2635.

Campillo, Nuria E., and J. A. Paez. "Cannabinoid system in neurodegeneration: new perspectives in Alzheimer's disease." Mini reviews in medicinal chemistry 9.5 (2009): 539-559.

Chaplan, S. R., et al. "Quantitative assessment of tactile allodynia in the rat paw." Journal of neuroscience methods 53.1 (1994) 55-63.

Chen, B., et al. "Effect of synthetic cannabinoid HU210 on memory deficits and neuropathology in Alzheimer's disease mouse model." Current Alzheimer Research 7.3 (2010): 255-261.

Davis, Tyler A., Todd K. Hyster, and Tomislav Rovis. "Rhodium (III)-Catalyzed Intramolecular Hydroarylation. Amidoarylation, and Heck-type Reaction: Three Distinct Pathways Determined by an Amide Directing Group." Angewandte Chemie International Edition 52.52 (2013): 14181-18185.

Diaz, Philippe, et al. "Preparation of heterocyclic diaryl compounds and pharmaceutical and cosmetic compositions containing them" Centre International de Recherches Dermatologiques Galderma, pp. 1-8.

Ex parte quayle for U.S. Appl. No. 12/668,840, filed Mar. 2, 2010, dated Sep. 14, 2012, pp. 1-4.

Ferandin, Yoan, et al. "3'-substituted 7-halogenoindlrubins, a new class of cell death inducing agents." Journal of medicinal chemistry 49.15 (2006): 4638-4649.

Gatley, S. John, et al. "123 I-labeled AM251: a radioiodinated ligand which binds in vivo to mouse brain cannabinoid CB 1 receptors." European journal of pharmacology 307.3 (1996): 331-338.

Giblin, Gerard MP, et al. "Discovery of 2-[(2, 4-dichlorophenyl) amino]-N-[(tetrahydro-2 H-pyran-4-yl) methyl]-4-(trifluoromethyl)-5-pyrimidinecarboxamide, a selective CB2 receptor agonist for the treatment of inflammatory pain." Journal of medicinal chemistry 50.11 (2007): 2597-2600.

Herzberg, U., et al. "The analgesic effects of R (+)-WIN 55.212-2 mesylate, a high affinity cannabinoid agonist. in a rat model of neuropathic pain." Neuroscience letters 221.2 (1997): 157-160.

Karl, Tim, et al. "The therapeutic potential of the endocannabinoid systems for Alzheimer's disease." Expert opinion on therapeutic targets 16.4 (2012): 407-420.

Kathuria, Satish, et al. "Modulation of anxiety through blockade of anandamide hydrolysis." Nature medicine 9.1 (2003): 76-81.

Kehl, Lois J., et al. "cannabinoid agonist differentially attenuates deep tissue hyperalgesia in animal models of cancer inflammatory muscle pain." Pain 103.1 (2003): 175-186.

MacCarrone, Mauro, et al. "The Endocannabinoid System in Human Keratinocytes Evidence That Anandamide Inhibits Epidermal Differentiation Through CB1 Receptor-Dependent Inhibition of Protein Kinase C, Activating Protein-1, and Transglutaminase." Journal of Biological Chemistry 278.36 (2003): 33896-33903.

Maresz, Katarzyna, et al. "Direct suppression of CNS autoimmune inflammation via the cannabinoid receptor CB1 on neurons and CB2 on autoreactive T cells." Nature medicine 13.4 (2007): 492-497.

Meda, Lucia, Pierluigi Baron, and Guglielmo Scarlato. "Glial activation in Alzheimer's disease: the role of Aβ and its associated proteins." Neurobiology of aging 22.6 (2001): 885-893.

Munro, Sean, Kerrie L. Thomas, and Muna Abu-Shaar. "Molecular characterization of a peripheral receptor for cannabinoids." (1993): 61-65.

Naguib, Mohamed, et al. "Prevention of paclitaxel-induced neuropathy through activation of the central cannabinoid type 2 receptor system." Anesthesia and analgesia 114.5 (2012): 1104.

Non Final Office Action for U.S. Appl. No. 14/611,499, filed Feb. 2, 2015, dated Jul. 7, 2015, pp. 1-5.

Onaivi, Emmanuel S., "Discovery of the presence and functional expression of cannabinoid CB2 receptors in brain." Annals of the New York Academy of Sciences 1074.1 (2006): 514-536.

Perry, V. High, James AR Nicoll, and Clive Holmes. "Microglia in neurodegenerative disease." Nature Reviews Neurology 6.4 (2010) 193-201.

Pertwee, Roger G. "Emerging strategies for exploiting cannabinoid receptor agonists as medicines." British journal of pharmacology 156.3 (2009): 397-411.

Pertwee, Roger G. "Cannabinoid receptors and pain." Progress in neurobiology 63.5 (2001): 569-611.

Polomano, Rosemary C., et al. "A painful peripheral neuropathy in the rat produced by the chemotherapeutic drug, paclitaxel." Pain 94.3 (2001): 293-304.

(56) References Cited

OTHER PUBLICATIONS

Ramirez, Belén G., et al. "Prevention of Alzheimer's disease pathology by cannabinoids. neuroprotection mediated by blockade of microglial activation." The Journal of Neuroscience 25.8 (2005): 1904-191.
Response to Non Final Office Action for U.S. Appl. No. 14/611,499 dated Jul. 7, 2015, filed Oct. 2, 2015, pp. 1-6.
Response to Ex Parte Quayle Action for U.S. Appl. No. 12/668,840, mailed Sep. 14, 2012, filed Nov. 14, 2012, pp. 1-4.
Response to Restriction Requirement for U.S. Appl. No. 12/668,840, dated Feb. 9, 2012, filed Jul. 6, 2012, pp. 1-2.
Restriction Requirement for U.S. Appl. No. 12/666,840, filed Mar. 2, 2010, dated Feb. 9, 2012, pp. 1-8.
Ross, Ruth A. et al., "Agonist-inverse agonist characterization at CB1 and CB2 cannabinoid receptors of L759633, L759656 and AM630." British journal of pharmacology 126.3 (1999): 665-672
Salo, Outi MH, et al. "Virtual screening of novel CB2 ligands using a comparative model of the human cannabinoid CB2 receptor." Journal of medicinal chemistry 48.23 (2005): 7166-7171.
Schmid, Adrien W., Marina A. Lynch, and Caroline E. Herron. "The effects of IL-1 receptor antagonist on beta amyloid mediated depression of LTP in the rat CA1 in vivo." Hippocampus 19.7 (2009): 670-676.
Steffens, Sabine, et al. "Low dose oral cannabinoid therapy reduces progression of atherosclerosis in mice." Nature 434.7034 (2005): 782-786.
Stella, Nephi. "Cannabinoid signaling in glial cells." Glia 48.4 (2004): 267-277.
Szlosek-Pinaud, Magali, et al. "Efficient synthetic approach to heterocycles possessing the 3, 3-disubstituted-2, 3-dihydrobenzofuran skeleton via diverse palladium-catalyzed tandem reactions." Tetrahedron 63.16 (2007): 3340-3349.
Szlosek-Pinaud.Magali, et al. "Palladium-catalyzed cascade allylation/carbopalladation/cross coupling: a novel three-component reaction for the synthesis of 3, 3-disubstituted-2, 3-dihydrobenzofurans." Tetrahedron letters 44.48 (2003): 8657-8659.
Teixeira-Clerc, Fatima, et al. "CB1 cannabinoid receptor antagonism: a new strategy for the treatment of liver fibrosis." Nature medicine 12.6 (2006): 671-676.
Tran. T., M. Sutak, and K. Jhamandas. "Involvement of cannabinoid (CB 1)-receptors in the development and maintenance of opioid tolerance." Neuroscience 146.3 (2007): 1275-1288.
Vanecek, Jiri, "Cellular machanisms of melatonin action." Physiological reviews 78.3 (1998): 687-721.
Wang, Haibin, et al. "Aberrant cannabinoid signaling impairs oviductal transport of embryos." Nature medicine 10 10 (2004): 1074-1080.
Whiteside. G. T., G. P. Lee, and K. J. Valenzano. "The role of the cannabinoid CB2 receptor in pain transmission and therapeutic potential of small moleule CB2 receptor agonists." Current medicinal chemistry 14.8 (2007): 917-936.
Wu, Jiang, et al. "Activatino of the CB 2 receptor system reverses amyloid-induced memory deficiency." Neurobiology of aging 34.3 (2013): 791-804.
Wyss-Coray, Tony. "Inflammation in Alzheimer disease driving force, bystander or beneficial response?" Nature medicine 12.9 (2008): 1005-1015.
Torres, E et al. "Research on Neurochemistry" Apr. 26, 2010; Expanded Reporting p. 292.
PCT International Search Report and Written Opinion for PCT/US13/20184, dated Dec. 9, 2013, pp. 1-11.
Office Action for corresponding JP App. No. 2015-521828 dated Dec. 6, 2016, pp. 1-5.
Clark, Richard B., Brian J. Knoll, and Roger Barber. "Partial agonists and G protein-coupled receptor desensitization." Trends in pharmacological sciences 20.7 (1999): 279-286.
Cruickshank, John M. "Measurement and cardiovascular relevance of partial agonist activity (PAA) involving β1-and β2-adrenoceptors." Pharmacology & therapeutics 46.2 (1990): 199-242.
Kenakin, Terry. "Inverse, protean, and ligand-selective agonism: matters of receptor conformation." The FASEB Journal 15.3 (2001): 598-611.
McDevitt, Denis G. "β-Adrenoceptor blocking drugs and partial agonist activity." Drugs 25.4 (1983): 331-338.
Stephenson, R. P. "A modification of receptor theory." British journal of pharmacology 11.4 (1956): 379-393.

\* cited by examiner

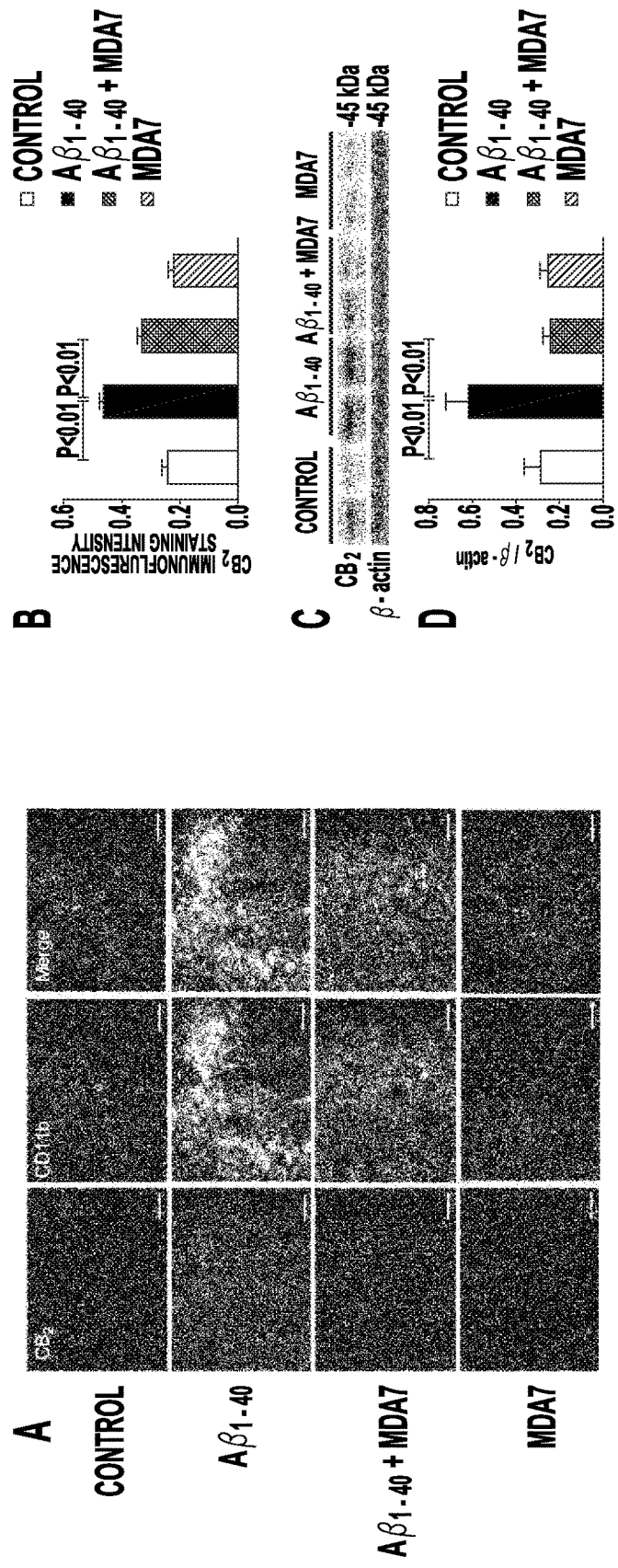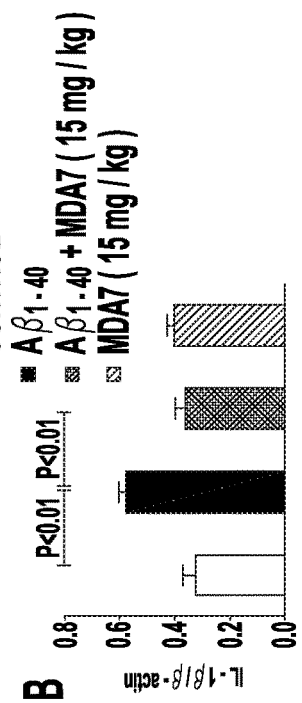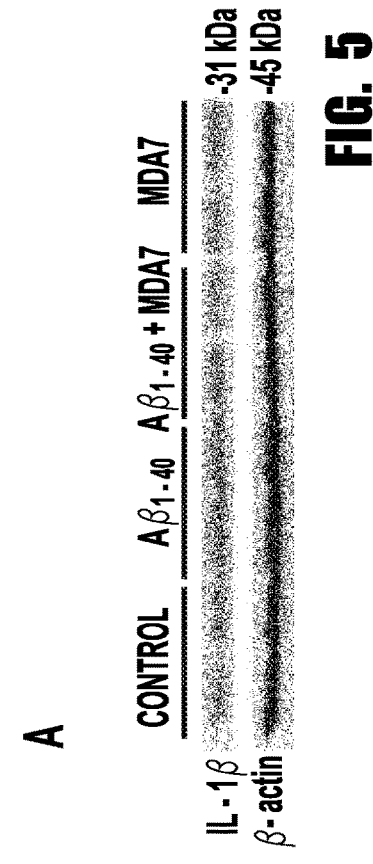
FIG. 4
FIG. 5

NEUROPROTECTIVE CB$_2$ RECEPTOR AGONISTS

CONTINUING APPLICATION DATA

This application claims the benefit of U.S. Provisional Application Ser. No. 61/671,277, filed Jul. 13, 2012, the disclosure of which is incorporated by reference herein

BACKGROUND

Alzheimer's disease (AD) is an age-dependent neurodegenerative disorder characterized by progressive loss of memory and cognitive function. The brains of patients with AD are characterized by extensive deposits of extracellular aggregation of amyloid-β (Aβ) peptides. These peptides form senile plaques and intracellular aggregation of hyperphosphorylated tau protein. The abnormal accumulation of amyloid fibrils result in the progressive loss of neuronal circuitry, impairment of the synaptic plasticity in the brain, and eventual memory deficiency. In addition, amyloid fibrils activate the inflammatory pathway, characterized by the activated microglia and astrocytes seen in the brains of patients with AD. It is possible that neuroinflammation could induce beneficial immune responses resulting in the phagocytosis of amyloid fibrils in an attempt to limit the development of the disease. Wyss-Coray, T., Nat. Med. 12, 1005-1015 (2006). However, prevailing evidence suggests that neuroinflammation could be a driving force in accelerating AD through the production of the proinflammatory chemokines, cytokines, and neurotoxins by the activated microglia and astrocytes in the brain. Perry et al., Nat. Rev. Neurol. 6, 193-201 (2010).

The cannabinoid receptor (CB) family currently includes two cloned metabotropic receptors: CB$_1$ (found predominantly in the brain), and CB$_2$ (found primarily in the peripheral immune system) and to a lesser degree in the central nervous system and microglia. In vivo injection of Aβ$_{1-42}$ into the hippocampus rat brain resulted in an increase in the endocannabinoid levels (van der Stelt et al., Cell. Mol. Life Sci. 63, 1410-1424 (2006)), and anandamide has been shown to prevent Aβ toxicity in cell culture (Milton, Neurosci. Lett. 332, 127-130 (2002)).

With the exception of a small population of neurons located in the brain stem and the cerebellum, healthy brain tissue does not express CB$_2$ receptors. Van Sickle et al., Science 310, 329-332 (2005). Rather, CB$_2$ receptors are upregulated in reactive microglial cells in AD, Huntington's disease, simian immunodeficiency virus-induced encephalitis, HIV encephalitis, and multiple sclerosis. In vitro studies demonstrated that CB$_2$-selective agonists blocked microglia-mediated neurotoxicity after Aβ is added to rat cortical co-cultures. Furthermore, intracerebroventricular administration of nonselective cannabinoid receptor agonist WIN 55,212-2 to rats prevented Aβ-induced microglial activation, cognitive impairment, and loss of neuronal markers. CB$_2$ agonists are neuroprotective and they have the advantage of lacking the psychotropic adverse effects normally seen with CB$_1$ agonists. Ramirez et al., J. Neurosci. 25, 1904-1913 (2005). In contrast, CB$_1$ agonists appear to have no beneficial effects on AD neuropathology and behavioral deficits in a mouse model of AD Chen et al., Curr. Alzheimer Res. 7, 255-261 (2010).

Studies show that in the settings of AD, microglia and astrocytes become fully reactive, initiating a proinflammatory cascade that results in the release of potentially neurotoxic substances, including cytokines, which lead to degenerative changes in neurons. CB$_2$ is also upregulated during this process. The inventors' previous work established 1-((3-benzyl-3-methyl-2,3-dihydro-1-benzofuran-6-yl) carbonyl) piperidine (MDA7) as a novel, blood-brain barrier-permeant, and highly selective CB$_2$ agonist. Diaz et al., Chemmedchem 4, 1615-1629 (2009). MDA7 lacks activity in CB$_2$ knockout mice and its effects in rats and C57BL/6 wild type mice are antagonized by CB$_2$ antagonists. Naguib et al., Anesth. Analg. 114, 1104-1120 (2012). The neuroprotective effect of MDA7 was found to be mediated through prevention of glial activation in vivo and in in vitro models. The potential effect of MDA7 in other glial-related pathophysiological conditions such as AD remains unexplored.

SUMMARY OF THE INVENTION

Cannabinoid type 2 (CB$_2$) agonists are neuroprotective and appear to play modulatory roles in neurodegenerative processes in Alzheimer's disease. The inventors studied the effect of MDA7—a novel selective CB$_2$ agonist that lacks psychoactivity—on ameliorating the neuroinflammatory process, synaptic dysfunction, and cognitive impairment induced by bilateral microinjection of amyloid-beta (Aβ$_{1-40}$) fibrils into the hippocampal CA1 area of rats. In rats injected with Aβ$_{1-40}$ fibrils, compared to the administration of intraperitoneal (i.p.) saline for 14 days, treatment with 15 mg/kg of MDA7 i.p. daily for 14 days (i) ameliorated the expression of CD11b (microglia marker) and GFAP (astrocyte marker), (ii) decreased the secretion of IL-1β, (iii) decreased the upsurge of CB$_2$ receptors, (iv) promoted Aβ clearance, and (v) restored synaptic plasticity, cognition and memory. The findings indicate that MDA7 is an innovative therapeutic approach for the treatment of Alzheimer's disease.

In one aspect, the invention provides a method of treating or preventing a neuroinflammatory and/or neurodegenerative disease in a subject by administering a pharmaceutically effective amount of a CB$_2$ receptor agonist to the subject. In some embodiments, the CB$_2$ receptor agonist comprises a compound according to Formula I:

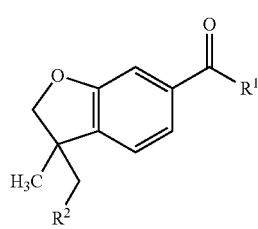

or a pharmaceutically acceptable salt thereof, wherein: R$^1$ is selected from the group consisting of cycloalkyl or heterocycloalkyl, any carbon atom of which may be optionally substituted; and R$^2$ is selected from the group consisting of aryl, cycloalkyl, aralkyl, and alkenyl, any carbon atom of which may be optionally substituted.

Another aspect of the invention provides a method of activating CB$_2$ receptors in microglia of a subject by administering a pharmaceutically effective amount of a CB$_2$ receptor agonist to the subject. In some embodiments, the subject has elevated levels of amyloid-β peptide in the brain. In other embodiments, activating the CB$_2$ receptors increases one or more of synaptic plasticity, cognition, or memory of the subject. In further embodiments, activating the CB$_2$ receptors decreases production of IL-1β by the microglia and inhibits MAPK. In a yet further embodiment, activating the $CB_2$ receptors increases glutamatergic neurotransmission in the subject.

BRIEF DESCRIPTION OF THE FIGURES

FIG. 4 provides graphs and images showing that administration of MDA7 attenuated $Aβ_{1-40}$ fibrils upregulated cannabinoid $(CB)_2$ receptor expression in the hippocampal CA1 area. (A) $CB_2$ staining and localization in the in the hippocampal CA1 area. Immunofluorescence images of $CB_2$ and CD11b in microglia and the coregionalization of $CB_2$ and microglia are shown. (B) No significant $CB_2$ expression was observed in the control group, but marked $CB_2$ expression was observed in the rats injected with $Aβ_{1-40}$ and treated with saline intraperitoneally (i.p.) for 14 days (P<0.01 vs. control) (n=20 sections from 5 animals per group). $CB_2$ expression was significantly decreased in the $Aβ_{1-40}$-injected rats receiving 15 mg/kg MDA7 treatment i.p. for 14 days. (C) Representative immunoblotting bands to show the expression of $CB_2$ receptor in hippocampal CA1 area in all groups; (D) plotted analysis of $CB_2$ immunoreactivity in hippocampus CA1 tissues in all groups. Note that MDA7 treatment significantly reversed the upsurge of $CB_2$ expression induced by $Aβ_{1-40}$ (P<0.01); n=6 per group. Statistical significance was determined by 1-way analysis of variance followed by Student-Newman-Keuls multiple range test. Data are shown as mean±standard error of the mean. Scale bar=40 μm.

FIG. 5 provides graphs and images showing that administration of MDA7 attenuated amyloid-β $(Aβ)_{1-40}$ fibrils upregulated interleukin (IL)-1β level in the hippocampal CA1 area. (A) Immunoblots of IL-1β reactivity in hippocampus CA1 tissues in all groups; (B) plotted analysis of IL-1β immunoreactivity in hippocampus CA1 tissues in all groups. Note that 15 mg/kg MDA7 treatment intraperitoneally (i.p.) for 14 days significantly reversed the increase of IL-1β protein expression induced by (P<0.01; n=5 per group; 1-way analysis of variance followed by Student-Newman-Keuls multiple range test). Data are shown as mean±standard error of the mean.

DETAILED DESCRIPTION OF THE INVENTION

Figure 1:
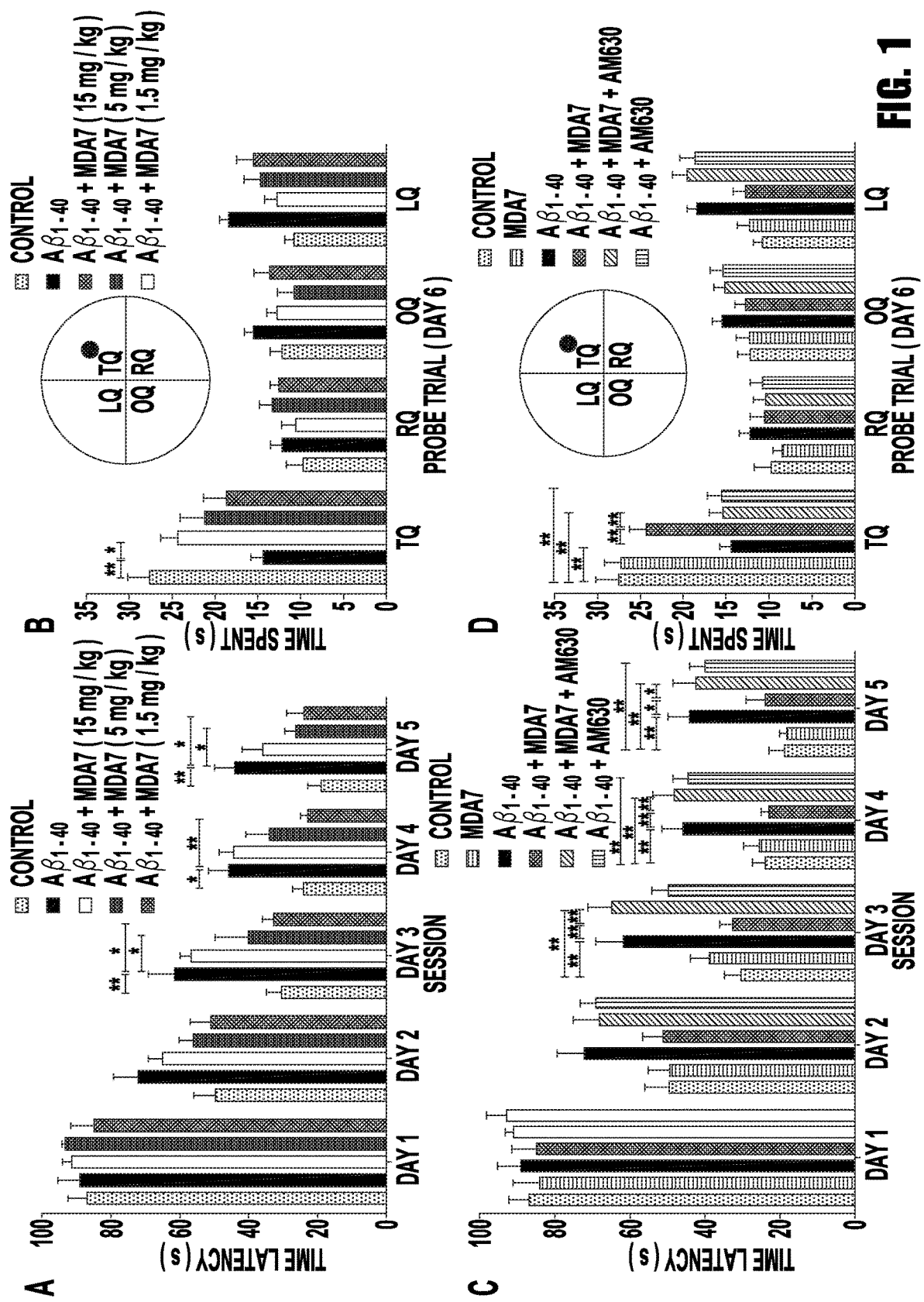
FIG. 1 provides bar graphs showing that administration of MDA7 attenuated amyloid fibril-impaired performance in the Morris water maze test. (A) MDA7 treatment decreases escape latency scores in the Morris water maze test in a dose-dependent manner. Animals injected with amyloid (Aβ) $Aβ_{1-40}$ fibrils and treated with MDA7 15 mg/kg intraperitoneally (i.p.) for 14 days had a significantly (P<0.05) shorter escape latency in the Morris water maze test than the animals injected with $Aβ_{1-40}$ fibrils and treated with saline i.p. for 14 days at days 3 and 5. In contrast, MDA7 1.5 mg/kg i.p. for 14 days did not result in any significant memory enhancement following $Aβ_{1-40}$ fibrils administration, however, the effect of the 5 mg/kg MDA7 dose was limited only to days 3 and 5. (B) The probe trial was performed on day 6 to determine the time spent in the target quadrant (TQ or platform quadrant) compared with right quadrant (RQ), opposite quadrant (OQ), and left quadrant (LQ). Rats injected with $Aβ_{1-40}$ fibrils and treated with MDA7 i.p. 15 mg/kg for 14 days spent the longest time in the TQ than animals injected with $Aβ_{1-40}$ and treated with saline i.p. for 14 days (P<0.05). (C) Rats injected with $Aβ_{1-40}$ fibrils and treated with saline i.p. for 14 days had a significantly extended escape latency in the Morris water maze test compared with that of the rats that received bilateral intracerebral microinjection of artificial cerebrospinal fluid and treated with saline i.p. (controls) or animals injected with $Aβ_{1-40}$ and treated with 15 mg/kg MDA7 i.p. for 14 days at days 3 to 5. Administration of AM630 prior to MDA7 treatment abrogated the observed effects of MDA7 indicating that the effects of MDA7 are mediated by stimulating cannabinoid $(CB)_2$ receptors. Furthermore, rats injected with $Aβ_{1-40}$ and received 5 mg/kg of AM630 i.p. for 14 days alone had cognitive impairment similar to those animals injected with $Aβ_{1-40}$ and treated with either saline i.p. or 5 mg/kg AM630 plus 15 mg/kg MDA7 i.p. for 14 days. The rats that received bilateral intracerebral microinjection of artificial cerebrospinal fluid and treated with saline i.p. or 15 mg/kg MDA7 for 14 days showed no significant difference in their escape latency values. (D) During the probe trial, the rats injected with $Aβ_{1-40}$ fibrils and treated with MDA7 15 mg/kg i.p. for 14 days spent the longest time in the TQ than animals injected with $Aβ_{1-40}$ and treated for 14 days with either saline i.p., AM630 alone, or AM630 plus MDA7 (P<0.01). Statistical significance was determined by repeated measures analysis of variance followed by Student-Newman-Keuls multiple range test.

The inventors have demonstrated that activation of central microglial CB$_2$ receptors by MDA7 promotes Aβ clearance, ameliorates Aβ-induced glial activation and production of IL-1β, and restores synaptic plasticity, cognition and memory. Accordingly, the present invention provides CB$_2$ receptor agonists that can be used for the treatment of neuroinflammatory and/or neurodegenerative diseases including as Alzheimer's disease.

Definitions

As used herein, the terms below have the meanings indicated. As used in the description of the invention and the appended claims, the singular forms "a", "an", and "the" are inclusive of their plural forms, unless contraindicated by the context surrounding such.

The term "alkenyl," as used herein, alone or in combination, refers to a straight-chain or branched-chain hydrocarbon radical having one or more double bonds and containing from 2 to 20, preferably 2 to 6, carbon atoms. Alkenylene refers to a carbon-carbon double bond system attached at two or more positions such as ethenylene [(CH=CH—), (—C::C—)]. Examples of suitable alkenyl radicals include ethenyl, propenyl, 2-methylpropenyl, 1,4-butadienyl and the like.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—).

The term "alkynyl," as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like.

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "arylalkyl" or "aralkyl," as used herein, alone or in combination, refers to an aryl group attached to the parent molecular moiety through an alkyl group.

The term "heteroaryl" means an aryl radical interrupted with one or more hetero atoms, such as a thiophenyl, thiazolyl or imidazolyl radical, optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 6 carbon atoms.

The term "cycloalkyl," or, alternatively, "carbocycle," as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydronapthalene, octahydronapthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocyclyl," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocyclyl" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocyclyl groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocyclyl groups may be optionally substituted unless specifically prohibited.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. This is true regardless of whether or not the enantiomers are shown in chemical formula representing the compounds. For example, if a compound that includes a chiral center is shown without any indication of stereochemistry, it is presumed to represent all possible stereoisomers of the compound. It should be understood that the term "compound" includes any or all of such forms, whether explicitly stated or not (although at times, "salts" are explicitly stated).

"Treat", "treating", and "treatment", etc., as used herein, refer to any action providing a benefit to a subject afflicted with a condition or disease such as Alzheimer's disease. Treatment can result in complete remission of the neurodegenerative disease, but can also include lesser effects, including improvement in the condition through lessening or suppression of at least one symptom, delay in progression of the disease, avoiding the development of additional symptoms in one known to be afflicted with Alzheimer's disease, etc.

Prevention, as used herein, refers to any action providing a benefit to a subject at risk of being afflicted with a condition or disease such as Alzheimer's disease, including avoidance of the development of Alzheimer's disease or a decrease of one or more symptoms of the disease should Alzheimer's disease develop. The subject may be at risk due to advanced age, as a result of family history, and/or from various other known risk factors.

"Pharmaceutically acceptable" as used herein means that the compound or composition is suitable for administration to a subject for the methods described herein, without unduly deleterious side effects in light of the severity of the disease and necessity of the treatment.

The term "pharmaceutically effective amount" is intended to qualify the amount of each agent which will achieve the goal of decreasing disease severity while avoiding adverse side effects such as those typically associated with alternative therapies. The pharmaceutically effective amount may be administered in one or more doses.

The inventors have determined that the $CB_2$ receptor functions in a negative-feedback loop and that the administration of a $CB_2$ agonist can promote clearance of A$\beta$, ameliorate the neuroinflammatory response to A$\beta$, and prevent A$\beta$-induced microglial and astrocyte activation, cytokine production, loss of synaptic plasticity, and cognitive impairment. Accordingly, one aspect of the invention provides a method of treating or preventing a neurodegenerative disease in a subject by administering a pharmaceutically effective amount of a cannabinoid receptor 2 ($CB_2$) receptor agonist to the subject. Cannabinoid receptors are a class of cell membrane receptors under the G protein-coupled receptor superfamily, and include subtypes $CB_1$ and $CB_2$. A $CB_2$ receptor agonist, as defined herein, is a compound that exhibits an $EC_{50}$ or $IC_{50}$ with respect to a $CB_2$ receptor activity of no more than about 100 µM and more typically not more than about 50 µM, as measured in the cannabinoid receptor assay described generally herein below. "$EC_{50}$" is that concentration of modulator which activates the activity of a cannabinoid receptor to half-maximal level. "$IC_{50}$" is that concentration of modulator which reduces the activity of a $CB_2$ receptor to half-maximal level.

A neurodegenerative disease is a disease involving progressive loss of structure or function of neurons, including death of neurons. There are a number of features commonly associated with various types of neurodegenerative disease, including protein misfolding, protein degradation pathways, mitochondrial dysfunction, and programmed cell death. Examples of neurodegenerative diseases include Alzheimer's disease, Parkinson's disease, Huntington's disease, and amylotrophic lateral sclerosis. In some embodiments, the disease is a neuroinflammatory disease. Neuroinflammatory diseases involve inflammation of neural tissue, and generally involve the activation of microglia and/or astroglia and the attendant expression of proinflammatory cytokines and chemokines. The term neuroinflammation has been well defined by those skilled in the art. O'Callaghan et al., Ann. N Y Acad Sci., 1139, 318-30 (2008).

In other embodiments, the disease involves elevated levels of amyloid-$\beta$ peptide in the brain of the subject. By "involves," it is meant that the A$\beta$ plays a role in the pathology of the disease. Elevated levels refer to levels higher than those found by in a healthy subject. There are a variety of ways to determine A$\beta$ levels, including immunostaining, ELISA, and atomic force microscopy. Amyloid beta (A$\beta$) is a peptide of 36-43 amino acids that is processed from the amyloid precursor protein (APP) that is best known as a component of amyloid plaques in association with Alzheimer's disease. Plaques are composed of a tangle of regularly ordered fibrillar aggregates called amyloid fibers. Similar plaques appear in some variants of Lewy body dementia and in inclusion body myositis (a muscle disease), while A$\beta$ can also form the aggregates that coat cerebral blood vessels in cerebral amyloid angiopathy.

In some embodiments, $CB_2$ receptor agonists are used to treat or prevent Alzheimer's disease. Alzheimer's disease (AD) is an age-dependent neurodegenerative disorder characterized by progressive loss of memory and cognitive function. The brains of patients with AD are characterized by extensive deposits of extracellular aggregation of (A$\beta$) peptides. The disease course is divided into four stages, with progressive patterns of cognitive and functional impairment, with include pre-dementia, early AD, moderate AD, and advanced AD. Symptoms of Alzheimer's disease include confusion, irritability, aggression, mood swings, trouble with language, and long-term memory loss. When a diagnosis of AD is suspected, the diagnosis can be confirmed by a brain scan and with tests that evaluate behaviour and thinking abilities. Computed tomography (CT), magnetic resonance imaging (MRI), single-photon emission computed tomography (SPECT), and positron emission tomography (PET) are examples of imaging technology that can be used to carry out brain scans in subjects suspected of having AD.

A variety of effective $CB_2$ receptor agonists have been developed. $CB_2$ receptor agonists include non-selective $CB_2$ receptor agonists and selective $CB_2$ receptor agonists. Examples of non-selective $CB_2$ receptor agonists include $\Delta^9$-tetrahydrocannabinol ($\Delta^9$-THC), (6aR)-trans-3-(1,1-dimethylheptyl)-6a,7,10,10$\alpha$-tetrahydro-1-hydroxy-6,6-dimethyl-6H-dibenzo[b,d]pyran-9-methanol (HU-210), (−)-cis-3-[2-hydroxy-4-(1,1-dimethylheptyl)phenyl]-trans-4-(3-hydroxypropyl)cyclohexanol (CP55940), (R)-(+)-[2,3-dihydro-5-methyl-3-(4-morpholinylmethyl)pyrrolo-[1,2,3- de]-1,4-benzoxazin-6-yl]-1-naphthalenylmethanone (R-(+)-WIN55212), N-arachidonoyl ethanolamine (anandamide), and 2-arachidonoyl glycerol.

Examples of selective $CB_2$ receptor agonists include 3-benzyl-3-methyl-2,3-dihydrobenzofuran-6-carboxylic acid-piperidine amide (MDA7), (2-methyl-1-propyl-1H-indol-3-yl)-1-napthalenylmethanone (JWH-015), 3-(1,1-dimethylbutyl)-6,6,9-trimethyl-6a,7,10,10α-tetrahydro-6H-benzo[c]chromene (JWH-133), HU-308, (2-iodo-5-nitrophenyl)-[1-(1-methylpiperidin-2-ylmethyl)-1H-indol-3-yl]-methanone (AM1241), GW405833, GW842166X, and O-1966. The structures and further information on selective and non-selective $CB_2$ receptor agonists are described by Guindon et al. (Guindon et al., Brit. J. Pharmacol, 153, 319-334 (2008)) and by Roger Pertwee (Pertwee, R, Brit. J. Pharmacol, 156, 397-411 (2009)), the disclosures of which are incorporated herein by reference. Additional $CB_2$ receptor agonists can be identified through high throughput screening of compounds developed from known chemical scaffolds, as described by Whiteside et al. (Whiteside et al., Curr Med Chem, 14(8), 917-36 (2007)), the disclosure of which is incorporated herein by reference.

Candidate $CB_2$ receptor agonists may be tested in animal models. For example, $CB_2$ receptor agonists can be tested in rats administered $A\beta_{1-40}$, as described herein. Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the Alzheimer's disease, including, for instance, increased $A\beta$ levels, loss of memory, decreased synaptic plasticity, or combinations thereof. For example, hippocampal LTP is used as a correlate for learning and memory and has emerged as a valuable model for studying mechanisms involved in cognitive deficits related to AD In some embodiments, the $CB_2$ receptor agonist comprises a compound according to Formula I:

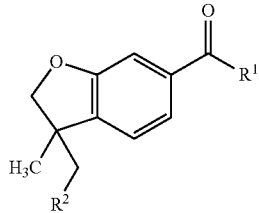

or a pharmaceutically acceptable salt thereof, wherein: $R^1$ is selected from the group consisting of cycloalkyl or heterocycloalkyl, any carbon atom of which may be optionally substituted; and $R^2$ is selected from the group consisting of aryl, cycloalkyl, aralkyl, and alkenyl, any carbon atom of which may be optionally substituted. In further embodiments, the $CB_2$ receptor agonist comprises an S isomer of a compound according to Formula I.

Structure activity studies have been conducted to demonstrate the activity of $CB_2$ receptor agonists according to Formula I. See Diaz et al., Chem Med Chem 4, 1615-1629 (2009), the disclosure of which is incorporated herein by reference. Some compounds were shown to have higher activity than others. For example, different activities can be obtained by varying the substituent at $R^2$. Accordingly, in some embodiments, $R^2$ is an aryl group, while in further embodiments $R^2$ is a phenyl group. Different activities can also be obtained by varying $R^1$. Accordingly, in some embodiments, $R^1$ is a heterocycloalkyl group, while in other embodiments, $R^1$ is a 1-piperidyl group.

In a preferred embodiment, the $CB_2$ receptor agonist is a compound according to formula II

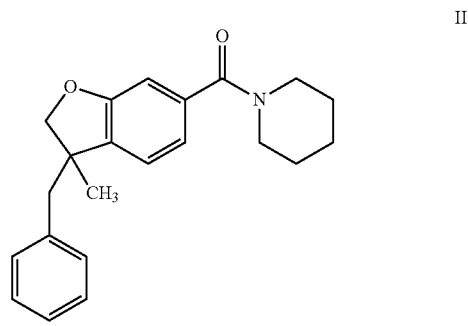 [SMILES: CC1(Cc2ccccc2)COc2cc(C(=O)N3CCCCC3)ccc21]

This compound has the chemical name 3-benzyl-3-methyl-2,3-dihydrobenzofuran-6-carboxylic acid-piperidine amide, and is also referred to herein as MDA7.

Additional studies have been carried out to determine if one of the enantiomers of MDA7 is more active than the other. While both enantiomers are active, the S enantiomer has been shown to display higher activity. See Luo et al, Tetrahedron Letters, 53(26), 3316 (2012), the disclosure of which is incorporated herein by reference. The structure of the S enantiomers ((S)-(3-benzyl-3-methyl-2,3-dihydrobenzofuran-6-yl)-piperidin-1-yl-methanone) is shown in formula III below:

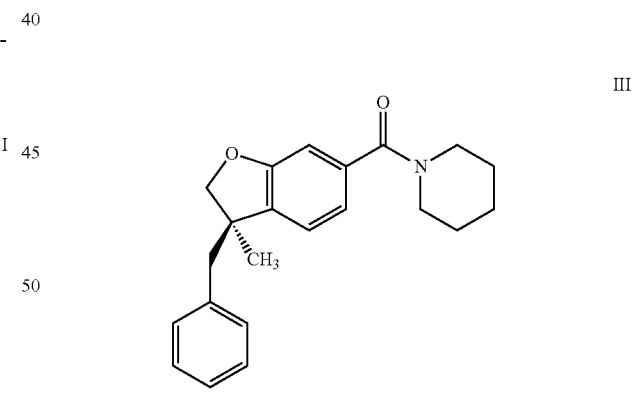

In another aspect, a method of activating $CB_2$ receptors in microglia of a subject by administering a pharmaceutically effective amount of a $CB_2$ receptor agonist to the subject is provided. The $CB_2$ receptor agonists include the specific and non-specific $CB_2$ receptor agonists described herein.

In some embodiments, the method of activating $CB_2$ receptors uses a $CB_2$ receptor agonist according to Formula I: In some embodiments, the $CB_2$ receptor agonist comprises a compound according to Formula I:

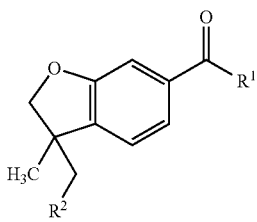

I or a pharmaceutically acceptable salt thereof, wherein: $R^1$ is selected from the group consisting of cycloalkyl or heterocycloalkyl, any carbon atom of which may be optionally substituted; and $R^2$ is selected from the group consisting of aryl, cycloalkyl, aralkyl, and alkenyl, any carbon atom of which may be optionally substituted.

In some embodiments, $R^2$ is an aryl group, while in further embodiments $R^2$ is a phenyl group. Different activities can also be obtained by varying $R^1$. In further embodiments, $R^1$ is a heterocycloalkyl group, while in other embodiments, $R^1$ is a 1-piperidyl group.

In a preferred embodiment, the $CB_2$ receptor agonist is a compound according to formula II

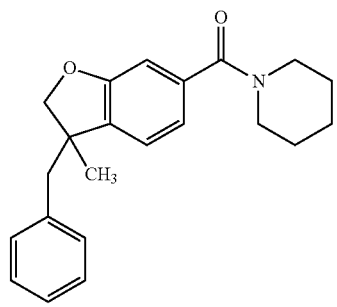

II

This compound has the chemical name 3-benzyl-3-methyl-2,3-dihydrobenzofuran-6-carboxylic acid-piperidine amide, and is also referred to herein as MDA7. In some embodiments, the $CB_2$ receptor agonist is the S enantiomer ((S)-(3-benzyl-3-methyl-2,3-dihydro-benzofuran-6-yl)-piperidin-1-yl-methanone).

In some embodiments of the method of activating $CB_2$ receptors in microglia of a subject, the subject has elevated levels of amyloid-β peptide in the brain. The inventors have shown that the presence of elevated levels of amyloid-β peptide in a subject induced the activation of astrocytes and microglia and upregulation of $CB_2$ receptors in the hippocampal CA1 area, and that treatment with the $CB_2$ receptor agonist MDA7 reversed this process. Because activation of the microglia results in inflammation, suppression of inflammation in neural tissue by reversing microglia activation can be used to treat or prevent neurodegenerative disease involving neuroinflammation.

The inventors have shown also that the activation of central microglial $CB_2$ receptors by MDA7 (i) promoted Aβ clearance, (ii) ameliorated Aβ-induced glial activation and production of IL-1β, and (iii) restored synaptic plasticity, cognition and memory. Accordingly, in some embodiments, the method of activating the $CB_2$ receptors can increase one or more of synaptic plasticity, cognition, or memory in a subject. Synaptic plasticity is the ability of the connection, or synapse, between two neurons to change in strength in response to either use or disuse of transmission over synaptic pathways. Since memories are postulated to be represented by vastly interconnected networks of synapses in the brain, synaptic plasticity is one of the important neurochemical foundations of learning and memory. Synaptic plasticity is generally measured as a change in an evoked electrophysiological response, such as transmitter release or change in relative electric potential. Definitions and methods of measuring cognition and memory capability in a subject are well known to those skilled in the art.

In another embodiment, activating the $CB_2$ receptors decreases production of IL-1β by the microglia. IL-1β is synthesized and released from the activated microglia and astrocytes in the brain and is actively involved in the development of amyloid-induced brain inflammation, impaired glutamatergic transmission and memory deficiency. The inventors demonstrated that the levels of interleukin 1β (IL-1β) from activated glial cells were significantly increased in the hippocampal CA1 area after microinjection of $Aβ_{1-40}$, and these increases were blunted by MDA7 treatment for 14 days. Decreasing IL-1β is important for at least the reason that IL-1β is an important mediator of neuroinflammation.

In a further embodiment, activating the $CB_2$ receptors increases glutamatergic neurotransmission in the subject. Glutamatergic neurotransmission is neurotransmission based on glutamate, which is a major excitatory neurotransmitter in the mammalian central nervous system. Niciu et al., Pharmacol Biochem Behav. 100(4), 656-664 (2012). Glutamatergic neurotransmission involves a variety of ionotropic and metabotropic receptors, such as NMDA receptors and AMPA/Kainate receptors. The inventors demonstrated that MDA7 effectively ameliorates glutamatergic transmission that had been impaired by $Aβ_{1-40}$.

The compounds of the invention can be used to provide prophylactic and/or therapeutic treatment. The compounds of the invention can, for example, be administered prophylactically to a subject in advance of the occurrence of a neurodegenerative disorder (e.g., Alzheimer's disease). Prophylactic (i.e., preventive) administration is effective to decrease the likelihood of the subsequent occurrence of neuroinflammatory or neurodegenerative disease in the subject, or decrease the severity of a neuroinflammatory or neurodegenerative disease that subsequently occurs. Prophylactic treatment may be provided to a subject that is at elevated risk of developing a neuroinflammatory and/or neurodegenerative disease, such as a subject with a family history of neuroinflammatory or neurodegenerative disease.

The compounds of the invention can also be administered therapeutically to a subject that is already afflicted by a neuroinflammatory or neurodegenerative disease. In one embodiment of therapeutic administration, administration of the compounds is effective to eliminate the neurodegenerative disease; in another embodiment, administration of the compounds is effective to decrease the severity of the neuroinflammatory or neurodegenerative disease or lengthen the lifespan of the subject so afflicted. The subject is preferably a mammal, such as a domesticated farm animal (e.g., cow, horse, pig) or pet (e.g., dog, cat). More preferably, the subject is a human, in which case the subject may also be referred to as a patient.

In some embodiments, the $CB_2$ receptor agonist may be administered in combination with one or more other agents known to be effective for treating Alzheimer's disease. By administration in combination with what is meant is that the compounds are administered to the subject in a contemporaneous manner. Administration in combination does not require that the agents be administered simultaneously or that they be formulated together, although in some embodiments this may be the case. Examples of additional agents known to be effective for treating Alzheimer's disease include acetylcholinesterase inhibitors such as tacrine, rivastigmine, galantamine and donepezil and the NMDA receptor antagonist memantine. Administration in combination with an additional anti-alzheimer's agent is also meant to include administration with subsequently developed anti-alzheimer's agents.

Administration and Formulation of the Compounds of the Invention

The present invention also provides pharmaceutical compositions that include compounds such as those defined by the formulae described herein as an active ingredient, and a pharmaceutically acceptable liquid or solid carrier or carriers, in combination with the active ingredient. Any of the compounds described above as being suitable for the treatment of cancer can be included in pharmaceutical compositions of the invention.

The compounds can be administered as pharmaceutically acceptable salts. Pharmaceutically acceptable salt refers to the relatively non-toxic, inorganic and organic acid addition salts of the compounds. These salts can be prepared in situ during the final isolation and purification of the compounds of the invention, or by separately reacting a purified compound of the invention with a suitable counterion, depending on the nature of the compound, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions include one or more compounds of the invention together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the compound, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The formulated compounds can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

One example of a formulation appropriate for administration through a parenteral route comprises 1.00 g of MDA7, 30.00 g of N-methyl pyrrolidone, 30.00 g of propylene glycol, 10.00 g of CREMOPHOR® ELP, 10.00 g of EtOH (95%), and 19.00 g of saline solution. Another example of formulation is based on hydroxypropyl-β-cyclodextrins (HPβCD) as described in Astruc-Diaz, F., McDaniel, S. W., Xu, J. J., Parola, S., Brown, D. L., Naguib, M., Diaz, P. 2013. In vivo efficacy of enabling formulations based on hydroxypropyl-β-cyclodextrins, micellar preparation, and liposomes for the lipophilic cannabinoid $CB_2$ agonist, MDA7. J Pharm Sci 102, 352-364.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parenteral (including subcutaneous, intramuscular, intraperitoneal, intratumoral, and intravenous) administration. A preferred form of administration is parenteral administration.

Formulations of the present invention suitable for oral administration may be presented as discrete units such as tablets, troches, capsules, lozenges, wafers, or cachets, each containing a predetermined amount of the active agent as a powder or granules, as liposomes containing the active compound, or as a solution or suspension in an aqueous liquor or non-aqueous liquid such as a syrup, an elixir, an emulsion, or a draught. Such compositions and preparations typically contain at least about 0.1 wt-% of the active agent. The amount of the $CB_2$ receptor agonist (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

A preferred method for administering a topical pharmaceutical formulation is a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, Reagents for Organic Synthesis, v. 1-19, Wiley, New York, (1967-1999 ed.); Alan R. Katritsky, Otto Meth-Cohn, Charles W. Rees, Comprehensive Organic Functional Group Transformations, v 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der organischen Chemie, 4, Aufl. Ed. Springer-Verlag, Berlin, Germany, including supplements (also available via the Beilstein online database)). In particular, methods for the preparation of a variety of $CB_2$ receptor agonists are described in U.S. patent application Ser. No. 12/668,840 and U.S. patent application Ser. No. 12/668,867, the disclosures of which are incorporated herein by reference.

The present invention is illustrated by the following examples. It is to be understood that the particular examples, materials, amounts, and procedures are to be interpreted broadly in accordance with the scope and spirit of the invention as set forth herein.

EXAMPLES

Example 1: Preparation of 3-benzyl-3-methyl-2,3-dihydrobenzofuran-6-carboxylic acid-piperidine amide (MDA7)

A) 4-Hydroxy-3-iodo-benzoic acid: 4-Hydroxybenzoic acid (0.037 mol, 5.1 g) was dissolved in 100 mL of methanol. One equivalent each of sodium iodide (0.037 mol, 5.54 g) and sodium hydroxide (0.037 mol, 1.48 g) was added, and the solution was cooled to 0° C. Aqueous sodium hypochlorite (64 ml, 4.0% NaOCl) was added dropwise over 75 min at 0-3° C. As each drop hit the solution, a red color appeared and faded almost instantly. The resulting colorless slurry was stirred for 1 h at 0-2° C. and then was treated with 40 mL of 10% aqueous sodium thiosulfate. The mixture was acidified by 4M aqueous HCl. A product crystallized and was filtered off to afford 1.1 g. Ethyl acetate (250 mL) was added, and the layers were separated. The organic layer was washed with brine (240 mL), water and then dried over $MgSO_4$. After evaporation of the solvent, 4.3 g of a white powder was obtained. The aqueous phase was acidified to pH 1. Ethyl acetate (250 mL) was added, and the layers were separated. The organic layer was washed with brine (240 mL), water and then dried over $MgSO_4$. After evaporation of the solvent, 8.22 g of a white powder was obtained.

B) Methyl 4-hydroxy-3-iodobenzoate: A solution of 3-iodo-4-Hydroxybenzoic acid (7.25 g, 27.4 mmol) and sulfuric acid (1.9 ml, 36 mmol) in methanol is stirred at 55° C. for 6 hours. TLC (dichloromethane): 30% of starting material. The solution is stirred 12 h at room temperature. TLC (dichloromethane): 10% of starting material and stirred at 55° C. for 2 h. After cooling, ethyl acetate (200 mL) was added and the mixture was adjusted to pH 3 using sodium bicarbonate. The organic layer was washed two times with water and then dried over $MgSO_4$. Filtration and rotary evaporation at 40° C. afforded a white solid. The solid was triturated with hexane, filtered off and dried under reduced pressure. M=4.47 g. Yield: 59%.

C) 4-Iodo-3-(2-methyl-allyloxy)-benzoic acid methyl ester: To a solution of methyl 3-hydroxy-4-iodobenzoate (1.5 g, 5.4 mmol) in anhydrous methyl ethyl ketone (60 mL) was added finely powdered Potassium carbonate (1.49 g, 10.78 mmol) followed by 3-bromo-2-methyl-propene (0.81 mL, 1.1 g, 8.15 mmol). The reaction mixture was heated at 70° C. for 4 h. The mixture was diluted filtrated, washed with water and dried over $MgSO_4$. Evaporation of the solvent and of the remaining bromopropene in vacuo afforded the requisite alkylated ester as a yellow oil. M: 1.4 g, Yield: 78%.

NMR (CDCl$_3$, $^1$H): 1.90 (3H, d, J=1.2 Hz), 194 (3H, s), 4.56 (2H, s), 5.06 (1H, d, J=1.2 Hz), 5.25 (1H, d, J=1.2 Hz), 7.38 (1H, dd, J=8.1 Hz, J=1.8 Hz), 7.44 (1H, d, J=1.8 Hz), 7.88 (1H, d, J=1.8 Hz)

D) 3-Benzyl-3-methyl-2,3-dihydro-benzofuran-6-carboxylic acid methyl ester: To a solution of 4-Iodo-3-(2-methyl-allyloxy)-benzoic acid methyl ester (455 mg, 1.37 mmol) in DMF (15 mL) were added Potassium carbonate (379 mg, 2.74 mmol), Tetrabutylammonium chloride (380 mg, 1.37 mmol), Palladium acetate (25.6 mg, 0.136 mmol) in DMF (5 mL) and Phenylboronic acid (200 mg, 1.64 mmol). The resulting mixture was stirred for 3 h at 115° C., cooled to room temperature, filtered over silica, washed with water, dried over $MgSO_4$ and concentrated. Column chromatography (silica gel, heptane/$CH_2Cl_2$: 4/6) afforded 368 mg (95%) of the title compound as a slightly brown oil which crystallize. Mp: 52° C.

NMR (CDCl$_3$, $^1$H): 1.38 (3H, s), 2.86 (1H, d, J=14 Hz), 2.93 (1H, d, J=14 Hz), 3.89 (3H, s), 4.12 (1H, d, J=8.7 Hz), 4.55 (1H, d, J=8.7 Hz), 6.93-6.98 (3H, m), 7.22-7.24 (3H, m), 7.38 (1H, d, J=1.2 Hz), 7.59 (1H, dd, J1=7.5 Hz, J2=1.2 Hz).

E) 3-Benzyl-3-methyl-2,3-dihydro-benzofuran-6-carboxylic acid: A mixture of 3-Benzyl-3-methyl-2,3-dihydro-benzofuran-6-carboxylic acid methyl ester (300 mg, 1.06 mmol), sodium hydroxide (260 mg, 6.5 mmol), ethanol (10 ml) and water (1 ml) in tetrahydrofuran (10 ml), is stirred for 12 h at room temperature. The reaction medium is acidified by adding a 1.2 M hydrochloric acid solution and extracted with ethyl acetate. The organic phase is washed with water, dried ($Na_2SO_4$), and concentrated in a rotary evaporator. The product is obtained as a white solid (300 mg, 100%). Mp: 165° C.

NMR ($CDCl_3$, $^1H$): 1.39 (3H, s), 2.87 (1H, d, J=14 Hz), 2.93 (1H, d, J=14 Hz), 4.14 (1H, d, J=8.7 Hz), 4.57 (1H, d, J=8.7 Hz), 6.96-7.00 (3H, m), 7.22-7.25 (3H, m), 7.45 (1H, d, J=1.2 Hz), 7.65 (1H, dd, J1=7.8 Hz, J2=1.2 Hz).

F) 3-benzyl-3-methyl-2,3-dihydrobenzofuran-6-carboxylic acid-piperidine amide: To a stirred suspension of the 3-Benzyl-3-methyl-2,3-dihydro-benzofuran-6-carboxylic acid (80 mg, 0.3 mmol) and piperidine (28 mg, 33 μL, 0.33 mmol) in dichloromethane (3 mL) and DMF (2 mL) were added O-(7-Azabenzotriazol-1-yl)-N,N,N',N'-tetramethyluronium hexafluorophosphate (HATU) (125 mg, 0.33 mmol) and then a solution of N,N-diisopropylethylamine (58 mg, 78 μL, 0.45 mmol, mL) in DMF (1 mL). The reaction mixture was stirred at ambient temperature for 18 h. The reaction medium is acidified by adding a 1.2 M hydrochloric acid solution and extracted with ethyl acetate. The organic phase is washed with water, dried ($MgSO_4$), and concentrated to give the amide which is purified by flash chromatography (AcOEt/heptane: 4/6) to afford 50 mg of a white solid (yield: 50%).

NMR ($CDCl_3$, $^1H$): 1.36 (3H, s), 1.54-1.67 (6H, m), 2.85 (1H, d, J=13.2 Hz), 2.90 (1H, d, J=13.2 Hz), 3.35 (2H, m), 3.68 (2H, m), 4.09 (1H, d, J=8.7 Hz), 4.53 (1H, d, J=8.7 Hz), 6.75 (1H, m), 6.88 (1H, dd, 31=7.5 Hz, J2=1.2 Hz), 6.94 (1H, d, J=7.5 Hz), 7.00 (2H, m), 7.21-7.24 (3H, m).

Example II: Activation of the $CB_2$ Receptor System Reverses Amyloid-Induced Memory Deficiency In this study, the inventors demonstrate that MDA7 exerts a neuroprotective effect by blunting neuroinflammatory processes that are pivotal for the development of Aβ-induced neurotoxicity. They found that MDA7 can: (1) promote Aβ clearance, (2) prevent increases in levels of glial fibrillary acidic protein (GFAP) in astrocytes and of CD11b in microglia (indicative of neuroinflammatory process activation) that are typically seen in the hippocampus of Aβ-injected rats; (3) decrease the production of interleukin (IL)-1β; (4) ameliorate the Aβ-mediated suppression of glutamatergic transmission in the hippocampus of Aβ-injected rats; and (5) prevent cognitive impairment on spatial memory performance using the Morris water maze test in the Aβ-injected rats. Because this $CB_2$ agonist prevented Aβ-induced neuroinflammation and its downstream consequence—synaptic plasticity and cognitive impairment—it was hypothesized that the $CB_2$ receptor functions in a negative-feedback loop and that its activation can induce Aβ clearance, and blunt neuroinflammatory responses and cognitive impairment induced by Aβ fibrils.

Material and Methods

Animals and treatment protocol. All animal procedures were approved by the Animal Care and Use Committee of Cleveland Clinic. Animals were housed the Institutional Biological Rodent Unit on a 12/12 h light/dark cycle with water and food pellets available ad libitum. Adult male Sprague-Dawley (Charles River, Wilmington, Mass.) rats weighing 200-250 g were used, and all experiments were performed during the light cycle.

Animals were divided into several groups (40-50 rats per group). The $Aβ_{1-40}$ group received bilateral intracerebral microinjection of $Aβ_{1-40}$ fibrils once and saline intraperitoneally (i.p.) daily for 14 days. The $Aβ_{1-40}$+MDA7 group received bilateral intracerebral microinjection of $Aβ_{1-40}$ fibrils once and 15 mg/kg MDA7 i.p. daily for 14 days. Other cohorts received smaller doses of MDA7 (5 mg/kg or 1.5 mg/kg) i.p. daily for 14 days to determine the dose-response characteristics for MDA7. In other groups, AM630 (a $CB_2$ antagonist) 5 mg/kg i.p. was administered daily for 14 days either alone ($Aβ_{1-40}$+AM630 group) or 15 min prior to MDA7 (15 mg/kg i.p.) administration ($Aβ_{1-40}$ MDA7+AM630 group) to rats injected with $β_{1-40}$ fibrils. MDA7 group and control group received bilateral intracerebral microinjection of artificial cerebrospinal fluid (130 mM NaCl, 2.6 mM KCl, 4.3 mM $MgCl_2$ and 1.8 mM $CaCl_2$) once and 15 mg/kg MDA7 or saline i.p. daily for 14 days, respectively. Intraperitoneal administration of AM630, MDA7 or saline started on the same day after intracerebral microinjection of $Aβ_{1-40}$. All drugs were prepared coded. Decoding was performed at the end of all experiments.

Microinjection of amyloid fibrils into the hippocampal CA1 area. Rats were anesthetized with sodium pentobarbital (45 mg/kg i.p.) and restrained in a stereotaxic apparatus. $Aβ_{1-40}$ fibrils were formed as described previously. Chacon, et al., Mol Psychiatry 9(10), 953-61 (2004). $Aβ_{1-40}$ fibrils (10 μg/3 μl) or 3 μl of artificial cerebrospinal fluid were injected stereotaxically and bilaterally into each hippocampus (coordinates; Bregma −3.5 mm anteroposterior, ±2.0 mm mediolateral, and −3.0 mm dorsoventral) using a 10 μl Hamilton syringe with a 27 G stainless steel needle at a rate of 0.5 μl/min. This experimental model has been used for studying AD. Ahmed, et al., Neuroscience 169(3), 1296-306 (2010).

Morris water maze test. A cohort of rats (n=10 per group) was tested 15 days after surgery as described by Chacon et al. (ibid). Testing was conducted in all groups at the same time of the day. The experimental apparatus consisted of a circular pool (120 cm in diameter, 45 cm high). An invisible platform (15 cm in diameter, 35 cm high) was placed 1.5 cm below the surface of the water. The water temperature was kept at 24-28° C. The pool was located in a test room, and many clues external to the maze were visible from the pool, which could be used by the rats for spatial orientation. The position of the cues was kept constant throughout the task. Each rat underwent four trials per day for five days. During each trial (memory acquisition), the rats were placed randomly at one of four fixed starting points and were allowed to swim for 120 s or until they escaped from the water by reaching the platform. The platform was located in the same position throughout the test in the middle of one quadrant. The start location was moved to a different quadrant in each trial so that no single start location was used in consecutive trials. In each training session, the latency to escape to the hidden platform was recorded. After the rats reached the platform, they were allowed to rest there for 20 seconds, and they then were removed from the pool. An inter-trial interval of at least 4 minutes was used to ensure that each rat's performance was not impaired by fatigue. After completing four trials, the rats were removed from the pool, dried and returned to their home cage. On Day 6, all rats were subjected to one probe trial (memory retrieval) in which the platform was removed, and each animal had 60 s to search the pool for the platform. All behavioral testing was performed by a single experimenter who was blinded to the different treatment groups. After the behavioral test, the rats were sacrificed, and the hippocampus tissues were collected for further study.

Hippocampal slice preparation. Brain slices containing hippocampus were prepared. Brain slices used for electrophysiological recording were obtained from all rats (n=10-12 rats per group) that had been subjected to the Morris water maze test. All rats were anesthetized with pentobarbital and then euthanized by decapitation. The brain was quickly removed and cut on a Vibratome (Leica VT-1000S) in cold (4° C.) physiological saline to obtain coronal slices (300 µm thick) containing the hippocampus. A single slice was submerged in a shallow recording chamber and perfused with warm (35° C.) physiological saline (126 mM NaCl, 2.5 mM KCl, 1.2 mM NaH$_2$PO$_4$, 1.2 mM MgCl$_2$, 2.4 mM CaCl$_2$, 11 mM glucose, and 25 mM NaHCO$_3$, saturated with 95% O$_2$ and 5% CO$_2$, pH 7.3-7.4). Slices were maintained at approximately 35° C. throughout the recording experiment.

Whole-cell patch clamp recordings in hippocampal slices. The hippocampal slices were allowed to recover for 1 h after which they were visualized using an upright microscope with infrared illumination. Whole-cell voltage-clamp recordings from the CA1 area were taken using an Axopatch 200B amplifier (Molecular Devices) with 2-4 MΩ glass electrodes containing the following internal solution (mM): K-gluconate or cesium methanesulfonate, 125; NaCl, 5; MgCl$_2$ 1; EGTA, 0.5; Mg-ATP, 2; Na$_3$GTP, 0.1; HEPES, 10; pH 7.3; 290-300 mOsmol. A seal resistance of ≥2 GΩ and an access resistance of 15-20 MΩ were considered acceptable. The series resistance was optimally compensated by ≥70% and constantly monitored throughout the experiments. The membrane potential was held at −70 mV, unless otherwise stated, throughout the experiment. Schaffer collateral-commissural fibers were stimulated by ultra thin concentric bipolar electrodes (FHC Inc., Bowdoinham, Me.), and the stimulus intensity was adjusted to evoke about 35% maximal stimulation unless specified. Excitatory postsynaptic currents (EPSCs) were recorded in the CA1 area in the presence of GABA$_A$ antagonist bicuculline (30 µM). The evoked EPSCs were filtered at 2 kHz, digitized at 10 kHz, and acquired and analyzed using Axograph X software. The amplitude of EPSCs was monitored for a baseline period of at least 15 min. If synaptic transmission was stable (<15% change in EPSC amplitude over 15 min), long-term potentiation (LTP) was induced by a single high-frequency electric stimuli train (100 Hz for 1 s). All electrophysiological experiments were performed at room temperature (23±2° C.).

Immunostaining. Immunostaining of the hippocampal slices was performed. Bie et al., J Neurosci 30(16), 5617-28 (2010). A cohort of rats (n=10-12 per group) were deeply anesthetized with 60 mg/kg sodium pentobarbital and perfused transcardially with 0.1 m PBS followed by 4% formalin. The brainstem was collected, postfixed in the same fixative for 4 h, and then cryoprotected in 30% sucrose in PBS for 3 days. Serial sections (30 µm, 15-20/rat) containing the hippocampal CA1 area were cut from the fixed brain. The sections were incubated for at least 1 h in 0.01 m PBS with 0.3% Triton X-100 plus 5% normal donkey serum. Primary and secondary antibodies were diluted in 0.01 m PBS with 0.3% Triton X-100 plus 1% bovine serum. Sections were processed overnight at 4° C. for double-labeling immunofluorescence using rabbit antibodies directed against CB$_2$ (1:500, Thermo Scientific, Rockford, Ill.), mouse monoclonal antibody against the microglial marker CD11b (1:200, Abcam, Cambridge, Mass.), and glial fibrillary acidic protein (GFAP) antibody (1:400; Abcam, Cambridge, Mass.). Other sections were processed overnight at 4° C. for immunofluorescence using Aβ$_{1-40}$ (11A50-B10) monoclonal antibody (1 µg/ml PBS, Covance San Diego Calif.). Then, the sections were incubated with a mixture of FITC- (1:500, Jackson ImmunoResearch, West Grove, Pa.) or Cy3-conjugated secondary antibodies (1:500, Jackson ImmunoResearch, West Grove, Pa.) for 1 h. Omission of primary or secondary antibodies resulted in no immunostaining. Three to six sections from each rat were randomly selected and were analyzed using Leica DMLB fluorescence microscope (Leica Microsystems Wetzlar GmbH, Germany) by one investigator, who was blinded to the origin of tissue being examined. Images were quantified using MCID Core software version 7.0 (InterFocus Imaging Ltd, Cambridge, England).

Protein extraction and immunoblotting. The hippocampal CA1 tissues from the rats in all groups (n=10-12 rats per group) were gently homogenized in ice-cold lysis buffer containing 50 mM Tris-Cl, 150 mM NaCl, 0.02 mM NaN$_2$, 100 µg/ml phenylmethyl sulfonyl fluoride, 1 µg/ml aprotinin, 1% Triton X-100 and proteinase inhibitor cocktail. The lysates were centrifuged at 14,000 rpm for 10 min at 4° C., and the supernatant was used for SDS-polyacrylamide gel electrophoresis. Protein concentrations were determined by using the Bio-Rad (Hercules, Calif.) protein assay kit.

The samples were treated with SDS sample buffer at 95° C. for 5 min, loaded on a 7.5% SDS-polyacrylamide gel, and blotted to a nitrocellulose membrane. The blots were incubated overnight at 4° C. with a rabbit polyclonal anti-CB$_2$ primary antibody (1:100; Santa Cruz Biotechnology, Inc., Santa Cruz, Calif.), monoclonal anti-CD11b antibody (1:1000; Abcam, Cambridge, Mass.), monoclonal anti-GFAP antibody (1:1000; Abcam, Cambridge, Mass.), goat polyclonal anti-IL-β antibody (1:300; Abcam, Cambridge, Mass.) or monoclonal anti-β-actin antibody (1:250; Santa Cruz Biotechnology, Inc.). The membranes were washed extensively with Tris-buffered saline and incubated with horseradish peroxidase-conjugated anti-mouse and anti-rabbit IgG or anti-goat IgG antibody (1:10,000; Jackson ImmunoResearch Laboratories Inc., West Grove, Pa.). The immunoreactivity was detected using enhanced chemiluminescence (ECL Advance Kit; Amersham Biosciences). The intensity of the bands was captured digitally and analyzed quantitatively with ImageJ software. The immunoreactivity of CB$_2$, CD11b, and GFAP was normalized to that of β-actin.

Compounds. Aβ peptide consisting of residues 1-40 of the human wild-type sequence (Aβ$_{1-40}$) was purchased from Bachem (Torrance, Calif., USA). AP-5 (D-2-amino-5-phosphonopentanoate), CNQX (6-cyano-2,3-dihydroxy-7-nitroquinoxaline), bicuculline, and other chemicals (NaCl, KCl, NaH$_2$PO$_4$, MgCl$_2$, CaCl$_2$, glucose, NaHCO$_3$, EGTA, Mg-ATP, Na$_3$GTP, HEPES and Triton-X 100) were purchased from Sigma Aldrich (St. Louis, Mo.) or Tocris (Ellisville, Mo.). AM630 (6-Iodo-2-methyl-1-[2-(4-morpholinyl)ethyl]-1H-indol-3-yl](4-methoxyphenyl)methanone) was purchased from Tocris (Ellisville, Mo.). MDA7 (hCB$_1$ Ki value>10,1000 nM; hCB$_2$ Ki value=422 nM; rCB$_1$ Ki value=2565 nM; rCB$_2$ Ki value=238 nM; EC$_{50}$ at hCB$_1$=not active, EC$_{50}$ at hCB$_2$=128 nM; EC$_{50}$ at rCB$_1$=not active; EC$_{50}$ at rCB$_2$=67 nM) was synthesized as previously described. Diaz, et al., Chem Med Chem 4(10), 1615-29 (2009).

Data analysis and statistics. The behavioral data were analyzed using repeated measures ANOVA followed by post hoc Student-Newman-Keuls multiple range test. Immunostaining and immunoblotting data were analyzed using one-way ANOVA followed by post hoc Student-Newman-Keuls multiple range test for group means. The evoked EPSC and LTP data were analyzed using repeated measures ANOVA followed by post hoc Student-Newman-Keuls multiple range test. All analyses were performed using the BMDP statistical package (Statistical Solutions, Saugus, Mass.).

Results were expressed as mean and SEM, and they were considered significant when $P<0.05$.

Results

Effect of activation of $CB_2$ on the behavioral test. Firstly, the effect of i.p. daily administration (for 14 days) of three different doses of MDA7 (1.5 mg/kg, 5 mg/kg, or 15 mg/kg) on cognitive impairment induced by $A\beta_{1-40}$ was determined. Repeated measures ANOVA identified a significant dose-dependent memory enhancing effect of MDA7 in the Morris water maze test (overall $F_{(4,45)}=6.86$, n=50, $P=0.0002$). Animals injected with $A\beta_{1-40}$ fibrils and treated with 15 mg/kg MDA7 i.p. for 14 days had a significantly shorter escape latency in the Morris water maze test than the animals injected with $A\beta_{1-40}$ fibrils and treated with i.p. saline for 14 days (FIG. 1A) at day 3 ($P<0.05$), day 4 ($P<0.05$), and day 5 ($P<0.05$). Similar observation was noted during the probe trial, in that the rats injected with $A\beta_{1-40}$ fibrils and treated with i.p. MDA7 15 mg/kg for 14 days spent the longest time in the target quadrant (TQ or platform quadrant) than animals injected with $A\beta_{1-40}$ and treated with i.p. saline for 14 days ($P<0.05$) (FIG. 1B). It was noted that the effect of 1.5 mg/kg MDA7 i.p. for 14 days did not result in any significant memory enhancement following $A\beta_{1-40}$ fibrils administration, however, the effect of the 5 mg/kg MDA7 dose was limited only to days 3 and 5 (FIG. 1A). Based on these data, the dose of 15 mg/kg of MDA7 was selected for further studies.

Repeated measures ANOVA for the data reported in FIG. 1C identified significant differences among the six groups (overall $F_{(5,54)}=8.10$, n=60, $P<0.0001$). The rats in the $A\beta_{1-40}$ group had a significantly extended escape latency in the Morris water maze test than those in $A\beta_{1-40}$+MDA7 group or the control group (FIG. 1C) at day 3 ($P<0.01$), day 4 ($P<0.01$), and day 5 ($P<0.01$). During the probe trial (FIG. 1D), rats in the $A\beta_{1-40}$+MDA7 group spent significantly longer time in the target quadrant than those in the $A\beta_{1-40}$ group ($P<0.01$). This indicated that MDA7 treatment was able to prevent the cognitive impairment on spatial memory performance induced by $A\beta_{1-40}$.

To confirm the $CB_2$-specific effect of MDA7, 5 mg/kg of AM630, a $CB_2$ antagonist, was administered i.p. daily for 14 days either alone or 15 min prior to MDA7 (15 mg/kg i.p.) administration to groups of rats injected with $A\beta_{1-40}$ fibrils. As shown in FIG. 1C, administration of AM630 prior to MDA7 treatment reversed the effect of MDA7 on the escape latency. Similar effect of AM630 was also noted in the probe test (FIG. 1D). Meanwhile, rats received AM630 alone i.p. (in the $A\beta_{1-40}$+AM630 group) did not show any improvement in spatial memory or probe test compared to that in the $A\beta_{1-40}$ group (FIGS. 1C and D). The different behavioral performances noted in this study were not attributable to the presence of motor deficits because all groups of rats exhibited similar swimming speeds (data not shown). The results indicated the effect of MDA7 on restoring cognition and memory was specifically mediated through the $CB_2$ receptor system.

MDA7 effectively ameliorates $A\beta_{1-40}$-induced glial activation in the hippocampal CA1 area. The accuracy of the microinjection was histologically verified afterwards. FIG. 2A shows an India ink-marked microinjection site in the hippocampal CA1 area demonstrating the preciseness of the injection site.

Prior studies have found an association between AD and glial cell activation. Akiyama et al., Neurobiol Aging 21(3), 383-421 (2000), Perry et al., Nat Rev Neurol 6(4) (2010). The possibility that MDA7's preventive effect on $A\beta_{1-40}$-induced microglial activation was mediated through modulation of glial activation was therefore considered. Increased expression of specific markers such as CD11b and GFAP have been associated with activation of microglia (Eng, J Neuroimmunol 8(4-6), 203-14 (1985)) and astrocytes, respectively.

Figure 2:
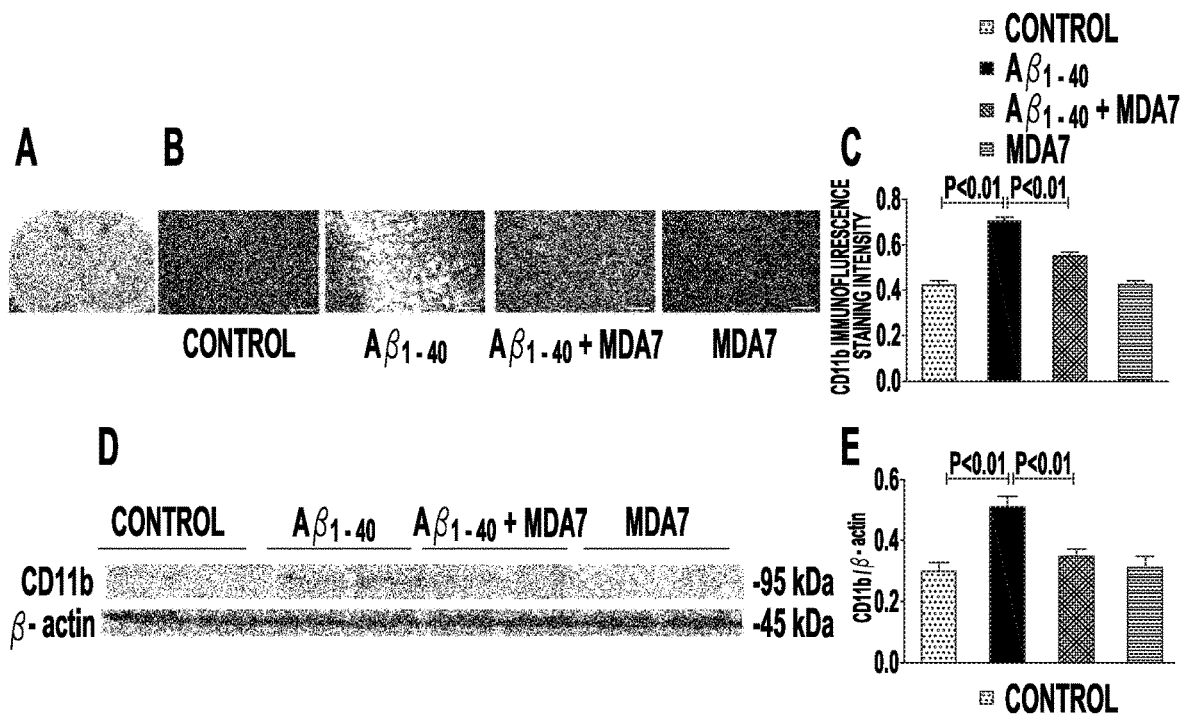
FIG. 2 provides graphs and images showing that administration of MDA7 attenuated amyloid fibrils-induced CD11b immunoreactivity in the hippocampal CA1 area. (A) Coronal rat brain section showing hippocampal ink injection: India ink was injected to confirm that the injection procedure was accurate and that the material was injected specifically into the hippocampal CA1 area of the rat. (B) Immunofluorescence images of CD11b immunoreactivity in various groups of rats in the hippocampal CA1 areas. (C) Analysis of CD11b immunofluorescence intensity (20 sections from 5 animals per group) showed that the amyloid-β $(Aβ)_{1-40}$-injected rats receiving MDA7 treatment intraperitoneally (i.p.) for 14 days had significantly less (P<0.01) immunofluorescence intensity than did the animals injected with $Aβ_{1-40}$ and treated with saline i.p. for 14 days. (D) Immunoblots of CD11b reactivity in hippocampus CA1 areas. (E) Analysis of CD11b immunoreactivity revealed significant increases in CD11b (P<0.01) intensities in animals injected with $Aβ_{1-40}$ and treated with saline i.p. for 14 days compared with that in the control group (n=5-7 per group). These changes were significantly (P<0.01) attenuated in the $Aβ_{1-40}$-injected rats receiving MDA7 treatment i.p. for 14 days. Note that treatment with MDA7 alone had no significant effect on the CD11B expression compared with the control rats. Statistical significance was determined by 1-way analysis of variance followed by Student-Newman-Keuls multiple range test.
Figure 3:
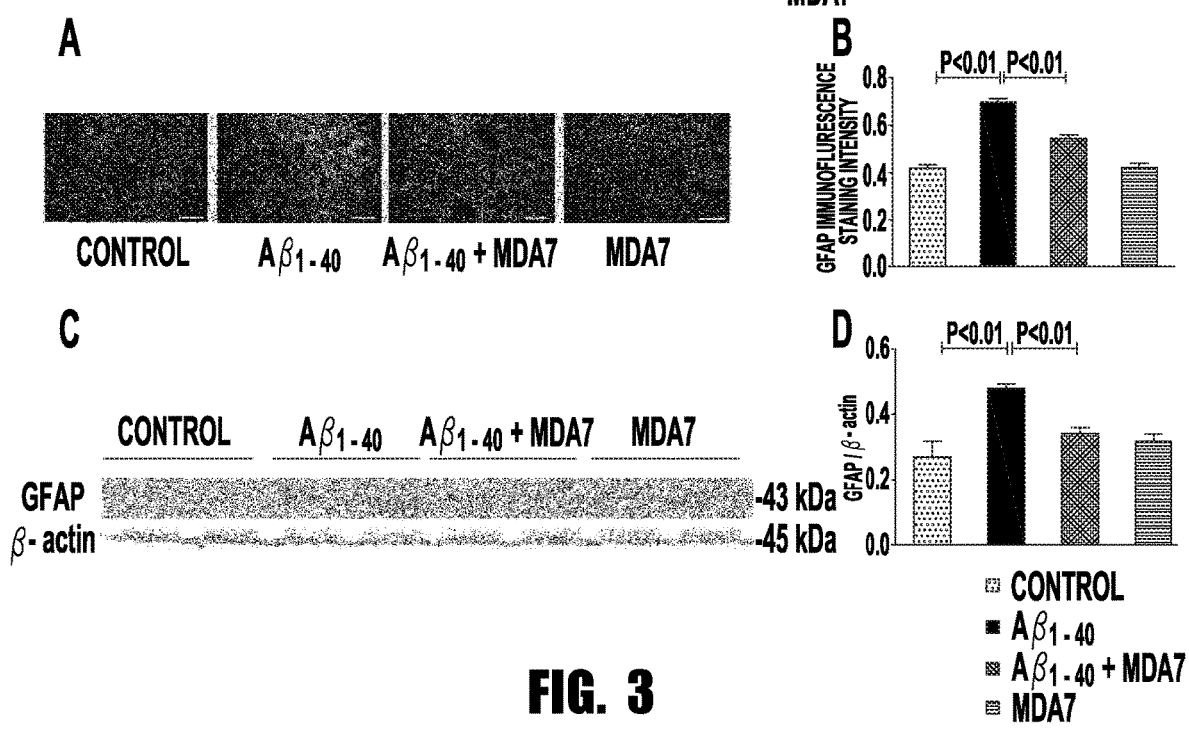
FIG. 3 provides graphs and images showing that administration of MDA7 attenuated amyloid fibrils-induced glial fibrillary acidic protein (GFAP) immunoreactivity in the hippocampal CA1 area. (A) Immunofluorescence images of GFAP immunoreactivity in various groups of rats in the hippocampal CA1 areas. (B) Analysis of GFAP immunofluorescence intensity (20 sections from 5 animals per group) showed that the amyloid-β $(Aβ)_{1-40}$-injected rats receiving 15 mg/kg MDA7 treatment intraperitoneally (i.p.) for 14 days had significantly less (P<0.01) immunofluorescence intensity than did the animals injected with $Aβ_{1-40}$ and treated with saline i.p. for 14 days. (C) Immunoblots of GFAP reactivity in the hippocampus CA1 areas. (D) Analysis of GFAP immunoreactivity revealed significant increases in GFAP (P<0.01) intensities in the rats injected with $Aβ_{1-40}$ and treated with saline i.p. for 14 days compared with those in the control group (n=5-7 per group). These changes were significantly (P<0.01) attenuated in the $Aβ_{1-40}$-injected rats receiving MDA7 treatment i.p. for 14 days. Note that treatment with 15 mg/kg MDA7 i.p. alone had no significant effect on the GFAP expression compared with control rats. Statistical significance was determined by 1-way analysis of variance followed by Student-Newman-Keuls multiple range test.

The impact of 15 mg/kg of MDA7 i.p. daily for 14 days on $A\beta_{1-40}$-induced microglial and astrocyte activation was examined by comparing the levels of immunofluorescence staining and immunoblotting intensity for CD11b (FIG. 2) and GFAP (FIG. 3) in the hippocampal CA1 area of rats in the various treatment groups. Glial activation is characterized by an increase in the number and complexity of these cells (rounded cell bodies and thicker processes), resulting in an increase in both the number of labeled cells and the total integrated intensity of the labeled cells (FIGS. 2B and 3A). When the hippocampal CA1 areas were examined in the rats after microinjection of $A\beta_{1-40}$ and treatment with i.p. saline for 14 days, increased CD11b and GFAP immunoreactivity, enlarged cell mass, and increased cell complexity were noted in the microglia (FIGS. 2B and 2C, $F_{(3,76)}=243.2$, n=80 sections (3-5 sections per animal from 5 animals per group), one-way ANOVA followed by Student-Newman-Keuls multiple range test, $P<0.01$) and astrocytes (FIGS. 3A and 3B, $F_{(3,76)}=225.3$, n=80 sections (3-5 sections per animal from 5 animals per group), $P<0.01$), respectively, compared to the control group.

The protein expression of CD11b (FIGS. 3D and 3E, n=6 rats per group, $F_{(1,10)}=19.9$, one-way ANOVA followed by Student-Newman-Keuls multiple range test, $P<0.01$) and GFAP (FIGS. 3C and 3D, n=5 rats per group, $F_{(1,8)}=32.7$, $P<0.01$) was significantly higher in the rats injected with $A\beta_{1-40}$ and treated with i.p. saline for 14 days than in the control group rats. These results confirmed that $A\beta_{1-40}$-induced brain inflammation is characterized by the activation of microglia and astrocytes in the hippocampal CA1 area. The changes in CD11b and GFAP expression were significantly attenuated in the $A\beta$-injected rats that received 14 days of MDA7 i.p. treatment compared to the animals injected with $A\beta_{1-40}$ and treated with i.p. saline for 14 days (FIGS. 2D and 2E, n=6-7 rats per group, $F_{(1,11)}=16.1$, one-way ANOVA followed by Student-Newman-Keuls multiple range test, $P<0.01$) (FIGS. 3C and 3D, n=5 rats per group, $F_{(1,8)}=46.2$, $P<0.01$). Treatment with MDA7 alone had no significant effect on the CD11B or GFAP expression compared to the control rats.

MDA7 modulated $A\beta_{1-40}$-induced $CB_2$ receptor upregulation in the hippocampal CA1 area. Previous studies by the inventors established MDA7 as a potent and selective $CB_2$ agonist. Naguib, et al., Br J Pharmacol 155(7), 1104-16 (2008). Herein, the effect of $A\beta_{1-40}$ fibrils on the expression of $CB_2$ receptor in the hippocampal CA1 area was examined. It was found that expression of $CB_2$ receptors was enhanced with $A\beta_{1-40}$ administration (FIGS. 4A and B, $F_{(3,76)}=48.45$, n=80 sections (3-5 sections per animal from 5 animals per group), one-way ANOVA followed by Student-Newman-Keuls multiple range test, $P<0.01$ versus control group) and this expression is colocalized with the reactive microglia. Administration of 15 mg/kg MDA7 i.p. for 14 days to rats injected with $A\beta_{1-40}$ resulted in reduced $CB_2$ expression ($P<0.01$ versus rats injected with $A\beta_{1-40}$ and treated with i.p. saline for 14 days).

The immunoblotting studies revealed that $CB_2$ receptor expression in the rats that received microinjection of $A\beta_{1-40}$ and treatment with i.p. saline for 14 days (FIGS. 4C and 4D, n=5, $F_{(1,8)}=10.3$, one-way ANOVA followed by Student-Newman-Keuls multiple range test, $P<0.05$) was greater than that in the control rats. Furthermore, treatment with 15 mg/kg of MDA7 i.p. daily for 14 days significantly reversed this upsurge of $CB_2$ receptor expression induced by $A\beta_{1-40}$ fibrils (FIGS. 4C and 4D, n=5, $F_{(1,8)}$=19.1, one-way ANOVA followed by Student-Newman-Keuls multiple range test, P<0.01). MDA7 did have any effect on the $CB_2$ receptor expression in the control rats. These results represent an adaptation of brain $CB_2$ receptor induced by $A\beta_{1-40}$ fibrils and its modulation by the $CB_2$ agonist MDA7.

MDA7 attenuates IL-1β protein expression induced by $A\beta_{1-40}$ in the hippocampal CA1 area. To better understand the basis for MDA7's interference with Aβ-induced neuroinflammation, the impact of MDA7 treatment (15 mg/kg i.p. daily for 14 days) on proinflammatory cytokine IL-1β production was examined in the hippocampal CA1 area. In the brain, IL-1β is mostly synthesized and secreted from the activated microglia and astrocytes (Kettenmann et al., Physiol Rev 91(2), 461-553 (2011)), and it is implicated in the development of brain inflammation (Gabay et al., Nat Rev Rheumatol 6(4), 232-41 (2010)) and amyloid-induced memory deficiency (Schmid et al., Hippocampus 19(7), 670-6 (2009)). In the present study, in animals injected with $A\beta_{1-40}$ and treated with i.p. saline for 14 days showed significantly higher expression of the IL-1β protein in the hippocampal CA1 tissue (FIG. 5, n=5, $F_{(1,8)}$=63.3, one-way ANOVA followed by Student-Newman-Keuls multiple range test, P<0.01) than the control rats (n=5). Meanwhile, MDA7 treatment for 14 days in the rats injected with $A\beta_{1-40}$ significantly attenuated the upsurge of IL-1β induced by microinjection of amyloid fibrils (FIG. 5, n=5, $F_{(1,8)}$=34.6, P<0.01). The results indicate that the levels of IL-1β from activated glial cells were significantly increased in the hippocampal CA1 area after microinjection of $A\beta_{1-40}$, and these increases were blunted by MDA7 treatment for 14 days.

Figure 6:
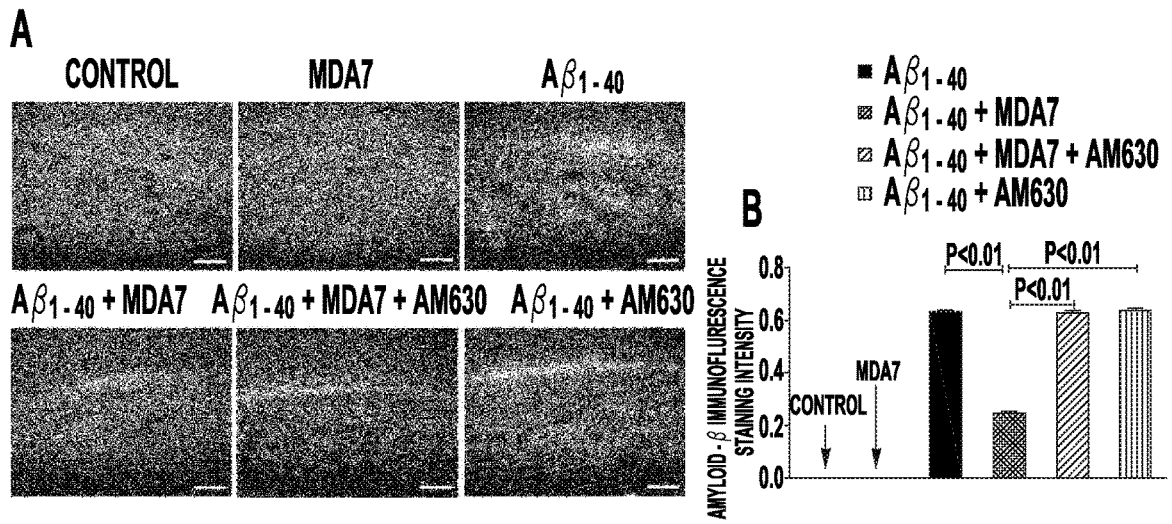
FIG. 6 provides graphs and images showing that the cannabinoid (CB)$_2$ agonist MDA7 induces amyloid-β (Aβ)$_{1-40}$ clearance. (A) Immunofluorescence images of Aβ$_{1-40}$ deposits in the hippocampal CA1 areas in different groups. (B) Rats injected with Aβ$_{1-40}$ and treated with 15 mg/kg MDA7 intraperitoneally (i.p.) for 14 days exhibited a reduction of the deposited Aβ peptide (P<0.01 vs. the rats injected with Aβ$_{1-40}$ and treated with saline i.p. for 14 days; n=20 sections from 5 animals per group) and this effect was abrogated by prior administration of 5 mg/kg AM630 i.p. for 14 days. Administration of 5 mg/kg AM630 i.p. alone has no effect on the clearance of the injected Aβ$_{1-40}$. Statistical significance was determined by 1-way analysis of variance followed by Student-Newman-Keuls multiple range test. Data are shown as mean±standard error of the mean. Scale bar=80 μm.

MDA7 effectively promotes the clearance of $A\beta_{1-40}$ injected in the hippocampal CA1 area. In vitro studies (Tolón et al., Brain Res 1283, 148-54 (2009)) have shown that the $CB_2$ activation induces removal of β-amyloid and this effect was blocked by $CB_2$ antagonists. The inventors thus hoped that MDA7 would enhance clearance mechanisms of the injected $A\beta_{1-40}$ in rats. MDA7 treatment for 14 days (15 mg/kg per day) in the rats injected with $A\beta_{1-40}$ induced removal of $A\beta_{1-40}$ (FIG. 6, $F_{(3,76)}$=707.07, n=80 sections (3-5 sections per animal from 5 animals per group), one-way ANOVA followed by Student-Newman-Keuls multiple range test, P<0.01) and this effect was abrogated by prior administration of 5 mg/kg AM630 i.p. for 14 days. The inventors also observed that administration of 5 mg/kg AM630 i.p. alone has no effect on the clearance of the injected $A\beta_{1-40}$. The results indicate that MDA7-mediated cognitive improvements are correlated with the enhanced clearance of Aβ peptide.

MDA7 effectively ameliorates $A\beta_{1-40}$-impaired glutamatergic transmission in the hippocampal CA1 area. Then, the input (stimulation intensity)-output (current amplitude) responses of the evoked EPSCs in the CA1 neurons were compared among all groups. As shown in FIGS. 7A and 7B, the amplitudes of evoked EPSCs were significantly less in the $A\beta_{1-40}$ group than that in the control group at all three stimulus intensities, indicating attenuated basal glutamatergic strength in the CA1 neurons. However, the amplitude of evoked EPSCs in the CA1 neurons from the rats injected with $A\beta_{1-40}$ in rats was restored by 15 mg/kg MDA7 i.p. treatment for 14 days in the $A\beta_{1-40}$+MDA7 group at all three stimulus intensities (FIGS. 7A and B). The basal glutamatergic strength in the hippocampal slices was not different between the control and MDA7 groups. These results indicated that administration of MDA7 significantly ameliorated the impaired basal glutamatergic strength induced by microinjection of $A\beta_{1-40}$ fibrils into the hippocampus.

In the hippocampus slice of the saline-injected rats, high frequency electric stimuli on the Schaffer collateral-commissural fibers induced significant synaptic potentiation in CA1 neurons that lasted more than one hour. The average LTPs were 210.5±18.6% and 224.7±2.2% at 30 min and 60 min after induction, respectively (n=12, repeated measures ANOVA followed by Student-Newman-Keuls multiple range test, P<0.01 when compared with baseline, FIGS. 7C and 7D). Meanwhile, in the hippocampus slice of the $A\beta_{1-40}$-injected rats, the intensity of LTP induced by high frequency electric stimuli was significantly attenuated. The average LTPs were 107.1±14.0% and 110.4±15.6% at 30 min and 60 min after induction, respectively (n=10, repeated measures ANOVA followed by Student-Newman-Keuls multiple range test, P<0.01 when compared with that in the saline-injected rats, FIGS. 7C and 7D). However, in the hippocampus slices from the Aβ+MDA7 group, the average LTPs were 214.5±23.6% and 195.7±21.8% at 30 min and 60 min after induction, respectively (n=9, repeated measures ANOVA followed by Student-Newman-Keuls multiple range test, P<0.01 when compared with that in the $A\beta_{1-40}$-injected rats, FIGS. 7C and 7D). Note that the administration of MDA7 alone failed to significantly affect the induction of LTP in the hippocampal slices of the control rats. These results indicated that administration of MDA7 significantly ameliorated the impaired hippocampal synaptic plasticity induced by microinjection of $A\beta_{1-40}$ fibrils.

DISCUSSION

The results reveal a promising potential role for the $CB_2$ agonist MDA7 in (i) promoting Aβ clearance; (ii) ameliorating Aβ-induced glial activation and cytokine production; and (iii) restoring of synaptic plasticity, cognition and memory. The effects of MDA7 were abrogated by prior administration of a $CB_2$ antagonist AM630. The administration of AM630 alone did not result in any beneficial effect on Aβ-related pathology. The present in vivo study confirmed that microinjection of $A\beta_{1-40}$ fibrils significantly (P<0.01) induced the activation of astrocytes and microglia and upregulation of $CB_2$ receptors in the hippocampal CA1 area and that MDA7 treatment reversed this process. The finding that microinjection of $A\beta_{1-40}$ in rats treated with i.p. saline was associated with increased $CB_2$ expression in the hippocampal CA1 area (FIG. 4) whereas treatment with the $CB_2$ agonist MDA7 ameliorated the effects of amyloid fibrils raises the possibility that the $CB_2$ receptor acts as a negative feedback regulator and its activation by MDA7 can serve to limit the extent of the neuroinflammatory response and the subsequent development of Aβ-induced neurotoxicity.

In the present study, microglial (CD11b) and astrocyte (FGAP) activation markers (measured on day 15) were significantly increased (P<0.01) in the hippocampal CA1 area after microinjection of $A\beta_{1-40}$ in rats treated with i.p. saline compared to controls (FIGS. 2 and 3). Aβ aggregates are potent neurotoxins and microglial activators (Cameron and Landreth, 2010). The results are consistent with previously published reports in which intracerebral microinjection of $A\beta_{1-42}$ in the hippocampus, frontal cortex, or intracerebroventricular administration of $A\beta_{25-35}$ in that the central administration of Aβ, is associated with microglia (Ramirez et al., J Neurosci 25(8), 1904-13 (2005)) and astrocyte activation. This neuroinflammatory process appears to contribute to and/or reflect neuronal dysfunction in the brain and is found to be inversely correlated with the cognitive function in AD (Edison et al., Neurobiol Dis 32(3), 412-9 (2008). Furthermore, in brain tissues from patients with AD, microglia and astrocyte activation, evidenced by cellular hypertrophy, increases in the expression of GFAP, astroglial S100B, and CD11b proteins, are routinely observed. Although micromolar concentrations of Aβ can induce direct toxicity to neurons, concentrations at nanomolar levels can induce neuronal loss through a microglia-mediated mechanism. It seems that the deposition of Aβ represents important trigger factors in glial activation (possibly via interaction with microglial surface receptors (El Khoury et al., Nature 382(6593), 716-9 (1996)) leading to an inflammatory reaction in the brain. Meda et al., Neurobiol Aging 22(6), 885-93 (2001). Although it has been reported that the administration of SR144525, a $CB_2$ antagonist, could have a role in decreasing $Aβ_{1-40}$-induced astrocyte activation, our data indicate that administration of 5 mg/kg AM630 (a $CB_2$ antagonist) i.p. for 14 days to rats injected with $Aβ_{1-40}$ failed to improve cognitive functions or induce Aβ clearance.

The results showed increased levels of IL-1β after bilateral microinjection of $Aβ_{1-40}$ in the hippocampus, and this increase was prevented by MDA7 treatment. $CB_2$ receptor activation has been shown to decrease the production of proinflammatory molecules in vitro in rat microglial cells, human microglial cells (Stella, Glia 48(4), 267-77 (2004)), and human astrocytes, and in animal models of perinatal hypoxia-ischemia, Huntington's disease, and paclitaxel-induced neuroinflammation. Naguib et al., Anesth Analg, 114(5):1104-20 (2012). IL-1β is synthesized and released from the activated microglia and astrocytes in the brain and is actively involved in the development of amyloid-induced brain inflammation, impaired glutamatergic transmission and memory deficiency. Intracerebroventricular administration of IL-1β significantly induced memory deficiency evidenced by impaired performance in several memory tasks. In the primary culture of hippocampal neurons, IL-1β (but not IL-10 or tumour necrosis factor-α) significantly down-regulated the surface expression and Ser831 phosphorylation of the AMPA receptor subunit GluR1, which plays an important role in synaptic plasticity. Antagonism of IL-1 receptor in the brain alleviated the impaired synaptic plasticity induced by Aβ. These previous reports established IL-1β, released from the activated microglia and astrocytes, as an important factor for the pathogenesis and development of Alzheimer's disease.

In the present study, an increased expression of $CB_2$ receptors in the hippocampal CA1 tissue in the rats was noted following microinjection of $Aβ_{1-40}$ fibrils. MDA7 appears to be effective in suppressing microglial and astrocyte activities and IL-1β production through activation of the $CB_2$ receptor system. Previous studies have demonstrated that $CB_2$ receptors expression in glia-associated plaques was increased in the postmortem AD brains. Ramirez et al., J Neurosci 25(8), 1904-13 (2005). Intracerebroventricular administration of a non-selective cannabinoid receptor agonist WIN 55,212-2 was effective in preventing $Aβ_{25-35}$-induced microglial activity. Different cannabinoids (WIN 55,212-2, HU-210, and JWH-113) blocked $Aβ_{1-40}$-induced activation of cultured microglial cells. Ramirez et al., Ibid. In primary microglial culture, $Aβ_{1-42}$-induced activation of $CB_2$ receptors and administration of JWH-015 (a $CB_2$ agonist) markedly suppressed microglial cytokines and nitric oxide production and attenuated CD40-mediated inhibition of microglial phagocytosis of $Aβ_{1-42}$. Ehrhart, et al., J Neuroinflammation 2, 29 (2005).

In vitro activation of $CB_2$ receptor facilitated the removal of native Aβ from human frozen tissue sections as well as removal of synthetic pathogenic peptide by a human macrophage cell line. Tolón et al., Brain Res 1283, 148-54 (2009). The data showed that activating $CB_2$ receptor system by MDA7 promoted $Aβ_{1-40}$ clearance (FIG. 6), possibly by restoring microglial phagocytic function. Microglia play an important role in promoting the clearance and phagocytosis of Aβ and there is an inverse relationship between cytokine production and Aβ clearance. However, as the AD progresses, microglia continue to produce proinflammatory cytokines, but lose their Aβ-clearing capabilities. Hickman et al., J Neurosci 28(33), 8354-60 (2008). Hence, the upregulation of microglial $CB_2$ receptor in the Alzheimer brain potentially positioned the $CB_2$ receptor as an endogenous protective mechanism to limit the neuroinflammation and pathological development in this disease. The beneficial effects of $CB_2$ agonist may not only rely on their ability to block Aβ-induced microglial activation, but also to restore microglial abilities to remove Aβ deposits.

Figure 7:
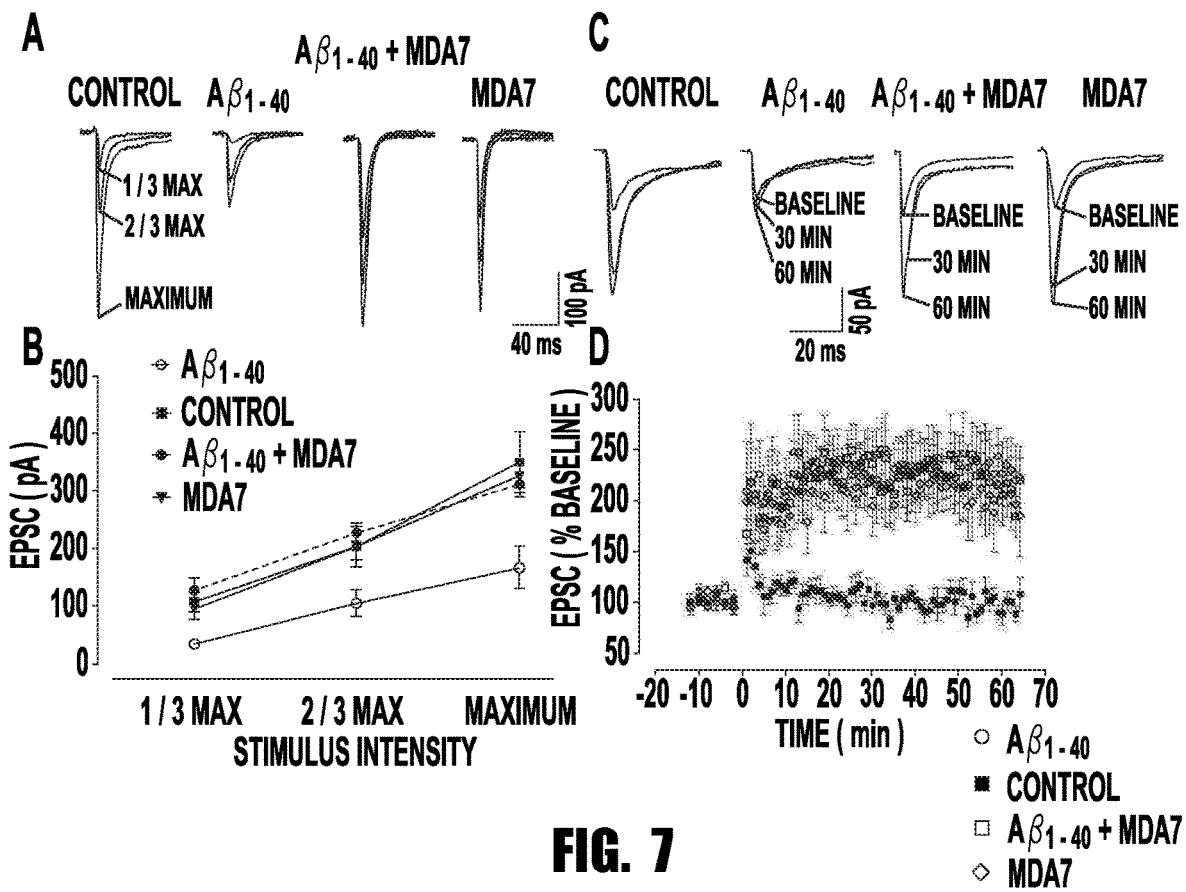
FIG. 7 provides graphs showing that systemic administration of 15 mg/kg MDA7 intraperitoneally (i.p.) for 14 days ameliorated amyloid-β (Aβ)$_{1-40}$-impaired basal glutamatergic strength and long-term potentiation (LTP) in the hippocampal CA1 slices. LTP was induced by the electric stimuli on the Schaffer collateral-commissural fibers at 100 Hz for 1 second. (A) Representative traces of evoked excitatory postsynaptic currents (EPSCs) at 3 graded stimulus intensities in all groups. (B) Input (stimulus intensity)-output (EPSC current) curve of evoked EPSCs in the CA1 neurons in all 4 groups (n=9-10 neurons per group). (C) Representative traces to show the evoked EPSCs at baseline, 30, and 60 minutes after electric induction in all 4 groups. (D) Time course of the LTP induction in the hippocampal CA1 neurons in all 4 groups (n=9-12 neurons from 4 to 5 rats per group). Statistical significance was determined by repeated measures analysis of variance followed by Student-Newman-Keuls multiple range test. Data are shown as mean±SEM. *P<0.05; **P<0.01 versus Aβ$_{1-40}$ and Aβ$_{1-40}$+MDA7 groups.

The behavioral deficits that were observed following hippocampal microinjection of $Aβ_{1-40}$ fibrils (FIG. 1B) correlated well with alteration in the hippocampal glutamatergic transmission (FIG. 7). The present study, for the first time, demonstrated that systemic administration of $CB_2$ agonist significantly ameliorated the impaired basal glutamatergic strength and electric stimuli-induced synaptic plasticity in the hippocampal CA1 area and the memory deficiency induced by the local microinjection of $Aβ_{1-40}$ fibrils. It was previously reported that microinjection of amyloid fragments significantly attenuated basal glutamatergic strength in the hippocampus of rodents. Intracerebroventricular injection of Aβ-containing aqueous extracts of Alzheimer's disease brain significantly inhibited high-frequency electric stimuli-induced LTP—a form of synaptic plasticity—in the rat hippocampus. Hippocampal LTP is used as a correlate for learning and memory and has emerged as a valuable model for studying mechanisms involved in cognitive deficits related to AD. Administration of exogenous Aβ into the hippocampus significantly lowered the performance in the memory tasks, such as the water maze, in rats. Consistently, in the present study, an impaired electric stimuli-induced LTP and basal glutamatergic strength and extended escape time in the Morris water maze test were observed in the rats 15 days after the microinjection of $Aβ_{1-40}$ fibrils in the rats treated with i.p. saline for 14 days. Interestingly, the impaired synaptic plasticity and memory deficiency were normalized by the systemic administration of 15 mg/kg MDA7 for 14 days.

In conclusion, activation of central microglial $CB_2$ receptors by MDA7 (i) promoted Aβ clearance, (ii) ameliorated Aβ-induced glial activation and production of IL-1β, and (iii) restored synaptic plasticity, cognition and memory. The presence of $CB_2$ receptors in microglia in the human AD brain indicate that the use of $CB_2$ receptor agonists such as MDA7 may represent a novel therapeutic method for the treatment of AD.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing possible mechanisms through with the compounds of the invention are effective, the inventors are not bound by theories described herein. The invention is not limited to the exact details shown and described, for variations obvious to one skilled in the art will be included within the invention defined by the claims.

What is claimed is:

1. A method of treating Alzheimer's disease in a subject by administering a pharmaceutically effective amount of a CB2 receptor agonist to the subject, wherein the CB2 receptor agonist comprises a compound according to Formula II

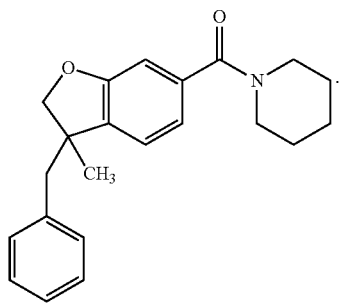

2. The compound of claim 1, wherein the compound is the S enantiomer.

3. The method of claim 1, wherein the CB2 receptor agonist is administered parenterally.

4. A method of activating CB2 receptors in central nervous system (CNS) microglia of a subject having Alzheimer's disease by administering a pharmaceutically effective amount of a CB2 receptor agonist to the subject, wherein the CB2 receptor agonist comprises a compound according to Formula II

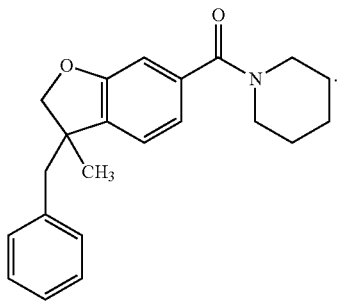

5. The method of claim 4, wherein the subject has elevated levels of amyloid-β peptide in the brain.

6. The method of claim 4, wherein activating the CB2 receptors increases one or more of synaptic plasticity, cognition, or memory of the subject.

7. The method of claim 4, wherein activating the CB2 receptors decreases production of IL-1β by the microglia.

8. The method of claim 4, wherein activating the CB2 receptors increases glutamatergic neurotransmission in the subject.

* * * * *